United States Patent
Ma et al.

(10) Patent No.: US 9,808,477 B2
(45) Date of Patent: *Nov. 7, 2017

(54) USE OF NOBILETIN IN CANCER TREATMENT

(71) Applicant: Macau University of Science and Technology, Macau (CN)

(72) Inventors: Wen-zhe Ma, Macau (CN); Sen-ling Feng, Macau (CN); Xiao-jun Yao, Macau (DJ); Zhong-wen Yuan, Macau (CN); Liang Liu, Macau (CN); Ying Xie, Macau (CN)

(73) Assignee: Macau University of Science and Technology, Macau (CN)

( * ) Notice: Subject to any disclaimer, the term of this patent is extended or adjusted under 35 U.S.C. 154(b) by 3 days.

This patent is subject to a terminal disclaimer.

(21) Appl. No.: 14/848,358

(22) Filed: Sep. 9, 2015

(65) Prior Publication Data

US 2017/0027901 A1    Feb. 2, 2017

Related U.S. Application Data

(60) Provisional application No. 62/198,137, filed on Jul. 29, 2015.

(51) Int. Cl.
  *A61K 31/352* (2006.01)
  *A61K 31/337* (2006.01)
  *A61K 45/06* (2006.01)
  *A61K 31/704* (2006.01)

(52) U.S. Cl.
  CPC .......... *A61K 31/704* (2013.01); *A61K 31/337* (2013.01); *A61K 31/352* (2013.01); *A61K 45/06* (2013.01)

(58) Field of Classification Search
  CPC .................. A61K 31/352; A61K 31/337
  See application file for complete search history.

(56) References Cited

FOREIGN PATENT DOCUMENTS

FR    CA 2337179 A1 *  1/2000  ........... A61K 31/352

OTHER PUBLICATIONS

Uesato et al., Planta Med., 2014, 80, p. 452-457, published online Mar. 31, 2014.*
Gupta et al.. Med. Chem. Res., 2014, 23, p. 1-15, published online May 16, 2013.*
Cancer multidrug resistance, Nature Biotechnology, 2000. 18 Suppl: p. IT18-20.
Gottesman, M.M., T. Fojo, and S.E. Bates, Multidrug resistance in cancer: role of ATP-dependent transporters. Nat Rev Cancer, 2002. 2(1): p. 48-58.
Gillet, J.P. and M.M. Gottesman, Mechanisms of multidrug resistance in cancer. Methods Mol Biol, 2010. 596: p. 47-76.
Coley, H.M., Overcoming multidrug resistance in cancer: clinical studies of p-glycoprotein inhibitors. Methods Mol Biol, 2010. 596: p. 341-58.
Baguley, B.C., Multidrug resistance in cancer. Methods Mol Biol, 2010. 596: p. 1-14.
Agarwal, R. and S.B. Kaye, Ovarian cancer: strategies for overcoming resistance to chemotherapy. Nat Rev Cancer, 2003. 3(7): p. 502-16.
Bansal, T., et al., Emerging Significance of Flavonoids as P-Glycoprotein Inhibitors in Cancer Chemotherapy. Journal of Pharmacy and Pharmaceutical Sciences, 2009. 12(1): p. 46-78.
No, J.H., Y.B. Kim, and Y.S. Song, Targeting nrf2 signaling to combat chemoresistance. J Cancer Prev, 2014. 19(2): p. 111-7.
Liu Z., G. Zhu, R.H. Getzenberg and R.W. Veltri, the upregulation of PI3K/Akt and MAP kinase pathways is associated with resistance of microtubule-targeting drugs in prostate cancer. J Cell Biochem, 2015.
Wu, G., et al., AKT/ERK activation is associated with gastric cancer cell resistance to paclitaxel. International Journal of Clinical and Experimental Pathology, 2014. 7(4): p. 1449-1458.
Mei, M., et al., A new 2alpha,5alpha,10beta,14beta-tetraacetoxy-4(20),11-taxadiene (SIA) derivative overcomes paclitaxel resistance by inhibiting MAPK signaling and increasing paclitaxel accumulation in breast cancer cells. PLoS One, 2014. 9(8): p. e104317.
Gao, Y., et al., Reversing effect and mechanism of soluble resistance-related calcium-binding protein on multidrug resistance in human lung cancer A549/DDP cells. Mol Med Rep, 2015. 11(3): p. 2118-24.
Karthikeyan, S. and S.L. Hoti, Development of Fourth Generation ABC Inhibitors from Natural Products: A Novel Approach to Overcome Cancer Multidrug Resistance. Anticancer Agents Med Chem, 2015.
Srivalli, K.M.R. and P.K. Lakshmi, Overview of P-glycoprotein inhibitors: a rational outlook. Brazilian Journal of Pharmaceutical Sciences, 2012. 48(3): p. 353-367.
Nogata, Y., et al., Flavonoid composition of fruit tissues of citrus species. Biosci Biotechnol Biochem, 2006. 70(1): p. 178-92.
Chen, J., et al., Nobiletin suppresses cell viability through AKT pathways in PC-3 and DU-145 prostate cancer cells. BMC Pharmacol Toxicol, 2014. 15: p. 59.
Murakami, A., et al., Inhibitory effect of citrus nobiletin on phorbol ester-induced skin inflammation, oxidative stress, and tumor promotion in mice. Cancer Res, 2000. 60(18): p. 5059-66.
Meiyanto, E., A. Hermawan, and Anindyajati, Natural products for cancer-targeted therapy: citrus flavonoids as potent chemopreventive agents. Asian Pac J Cancer Prev, 2012. 13(2): p. 427-36.
Yasuda, N., et al., Neuroprotective effect of nobiletin on cerebral ischemia-reperfusion injury in transient middle cerebral artery-occluded rats. Brain Res, 2014. 1559: p. 46-54.
Chen, C., et al., Antiproliferative and apoptosis-inducing activity of nobiletin against three subtypes of human breast cancer cell lines. Anticancer Res, 2014. 34(4): p. 1785-92.

(Continued)

*Primary Examiner* — Jonathan S Lau
(74) *Attorney, Agent, or Firm* — Eagle IP Limited; Jacqueline C. Lui

(57) ABSTRACT

The present invention discloses a pharmaceutical composition of treating multidrug resistance cancer, comprising a citrus methoxyflavone and a chemotherapeutic drug, in which the citrus methoxyflavone is nobiletin. A method of treating multidrug resistance cancer comprising administrating citrus methoxyflavone and a chemotherapeutic drug is also disclosed.

8 Claims, 17 Drawing Sheets
(14 of 17 Drawing Sheet(s) Filed in Color)

(56) References Cited

OTHER PUBLICATIONS

Morley, K.L., P.J. Ferguson, and J. Koropatnick, Tangeretin and nobiletin induce G1 cell cycle arrest but not apoptosis in human breast and colon cancer cells. Cancer Lett, 2007. 251(1): p. 168-78.

Yoshimizu, N., et al., Anti-tumour effects of nobiletin, a citrus flavonoid, on gastric cancer include: antiproliferative effects, induction of apoptosis and cell cycle deregulation. Aliment Pharmacol Ther, 2004. 20 Suppl 1: p. 95-101.

Takanaga, H., et al., Polymethoxylated flavones in orange juice are inhibitors of P-glycoprotein but not cytochrome P450 3A4. J Pharmacol Exp Ther, 2000. 293(1): p. 230-6.

Honda, Y., et al., Effects of grapefruit juice and orange juice components on P-glycoprotein- and MRP2-mediated drug efflux. Br J Pharmacol, 2004. 143(7): p. 856-64.

Patino, W.D., et al., Circulating transcriptome reveals markers of atherosclerosis. Proc Natl Acad Sci U S A, 2005. 102(9): p. 3423-8.

Chou, T.C., Drug Combination Studies and Their Synergy Quantification Using the Chou-Talalay Method. Cancer Research, 2010. 70(2): p. 440-446.

Van Breemen, R.B. and Y. Li, Caco-2 cell permeability assays to measure drug absorption. Expert Opin Drug Metab Toxicol, 2005. 1(2): p. 175-85.

Ding, P.R., et al., The Phosphodiesterase-5 Inhibitor Vardenafil Is a Potent Inhibitor of ABCB1/P-Glycoprotein Transporter. Plos One, 2011. 6(4).

Wang, Y.J., et al., Motesanib (AMG706), a potent multikinase inhibitor, antagonizes multidrug resistance by inhibiting the efflux activity of the ABCB1. Biochem Pharmacol, 2014. 90(4): p. 367-78.

Aller, S.G., et al., Structure of P-glycoprotein reveals a molecular basis for poly-specific drug binding. Science, 2009. 323(5922): p. 1718-22.

Ohnishi, H., et al., Inhibition of cell proliferation by nobiletin, a dietary phytochemical, associated with apoptosis and characteristic gene expression, but lack of effect on early rat hepatocarcinogenesis in vivo. Cancer Sci, 2004. 95(12): p. 936-42.

Shi, M.D., et al., Nobiletin attenuates metastasis via both ERK and PI3K/Akt pathways in HGF-treated liver cancer HepG2 cells. Phytomedicine, 2013. 20(8-9): p. 743-752.

Wang, X.J., et al., Nrf2 enhances resistance of cancer cells to chemotherapeutic drugs, the dark side of Nrf2. Carcinogenesis, 2008. 29(6): p. 1235-43.

Gao, A.M., et al., Chrysin enhances sensitivity of BEL-7402/ADM cells to doxorubicin by suppressing PI3K/Akt/Nrf2 and ERK/Nrf2 pathway. Chem Biol Interact, 2013. 206(1): p. 100-8.

Gao, A.M., et al., Apigenin sensitizes doxorubicin-resistant hepatocellular carcinoma BEL-7402/ADM cells to doxorubicin via inhibiting PI3K/Akt/Nrf2 pathway. Carcinogenesis, 2013. 34(8): p. 1806-14.

Wang, Z.W., Y.J. Huang, and J.Q. Zhang, Molecularly targeting the PI3K-Akt-mTOR pathway can sensitize cancer cells to radiotherapy and chemotherapy. Cellular & Molecular Biology Letters, 2014. 19(2): p. 233-242.

Evans, M., P. Sharma and N. Guthrie, Bioavailability of Citrus Polymethoxylated Flavones and Their Biological Role in Metabolic Syndrome and Hyperlipidemia. 2012: INTECH Open Access Publisher.

Manthey, J.A., et al., Pharmacokinetic study of nobiletin and tangeretin in rat serum by high-performance liquid chromatography-electrospray ionization-mass spectrometry. J Agric Food Chem, 2011. 59(1): p. 145-51.

Blagosklonny, M.V. and T. Fojo, Molecular effects of paclitaxel: myths and reality (a critical review). Int J Cancer, 1999. 83(2): p. 151-6.

Luo, G., X. Guan and L. Zhou, Apoptotic effect of citrus fruit extract nobiletin on lung cancer cell line A549 in vitro and in vivo. Cancer Biol Ther, 2008. 7(6): p. 966-73.

Giannakakou, P., et al., Low concentrations of paclitaxel induce cell type-dependent p53, p21 and G1/G2 arrest instead of mitotic arrest: molecular determinants of paclitaxel-induced cytotoxicity. Oncogene, 2001. 20(29): p. 3806-13.

Burris, H.A., 3rd, Overcoming acquired resistance to anticancer therapy: focus on the PI3K/AKT/mTOR pathway. Cancer Chemother Pharmacol, 2013. 71(4): p. 829-42.

Imada, K., et al., Nobiletin, a citrus polymethoxy flavonoid, suppresses gene expression and production of aggrecanases-1 and -2 in collagen-induced arthritic mice. Biochem Biophys Res Commun, 2008. 373(2): p. 181-5.

Ma, X., et al., Inhibitory effects of nobiletin on hepatocellular carcinoma in vitro and in vivo. Phytother Res, 2014. 28(4): p. 560-7.

\* cited by examiner

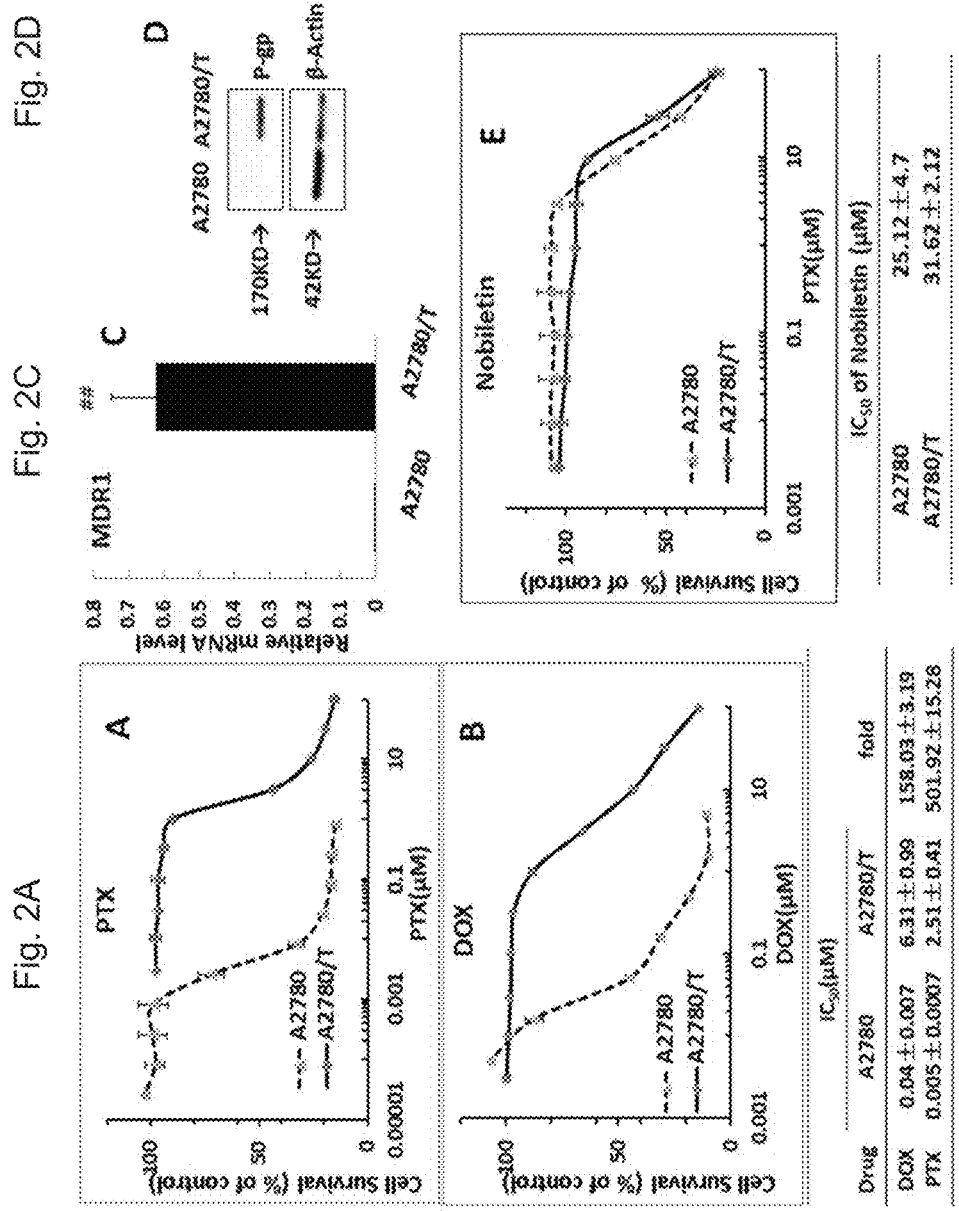

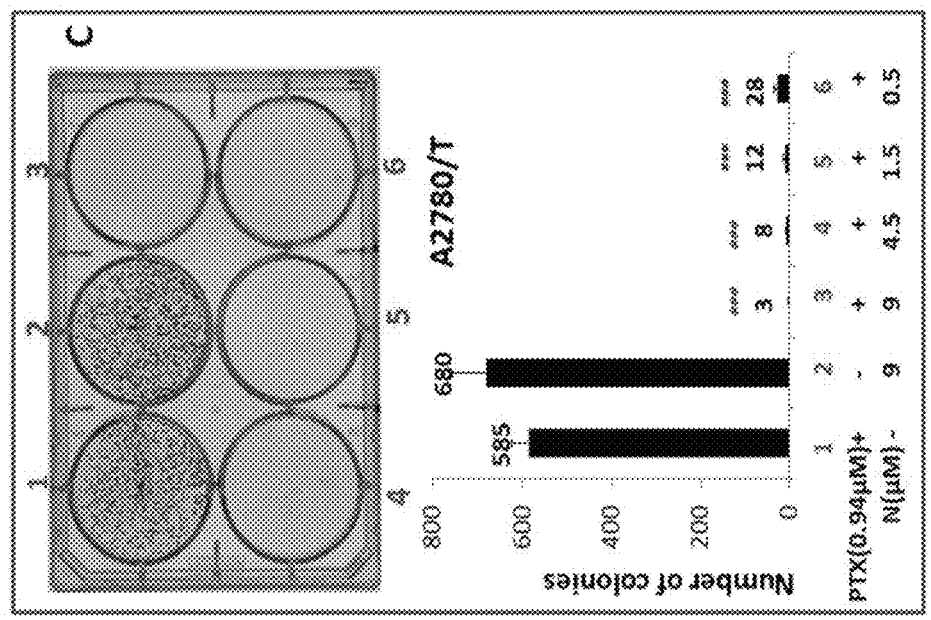
Fig. 3C
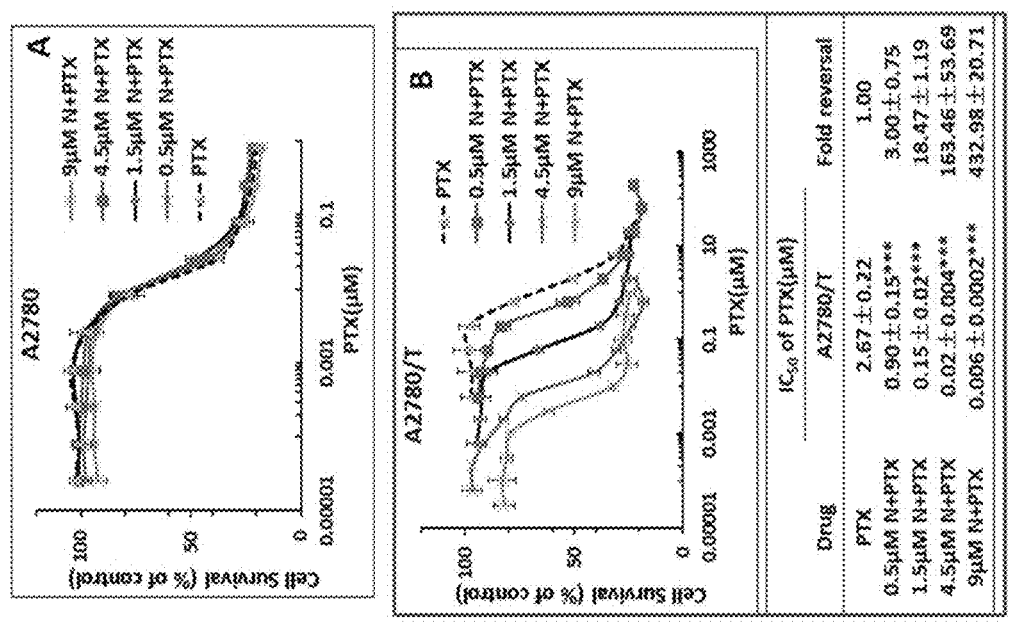
Fig. 3A
Fig. 3B

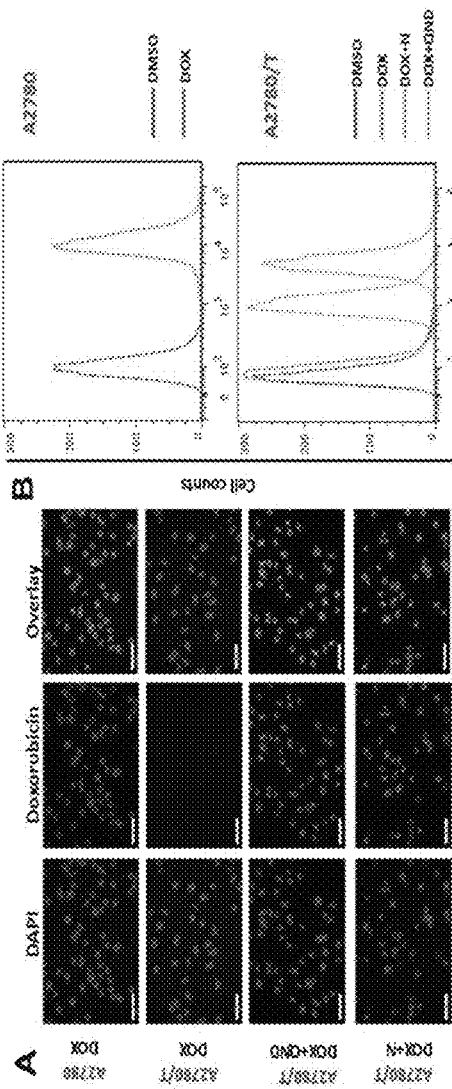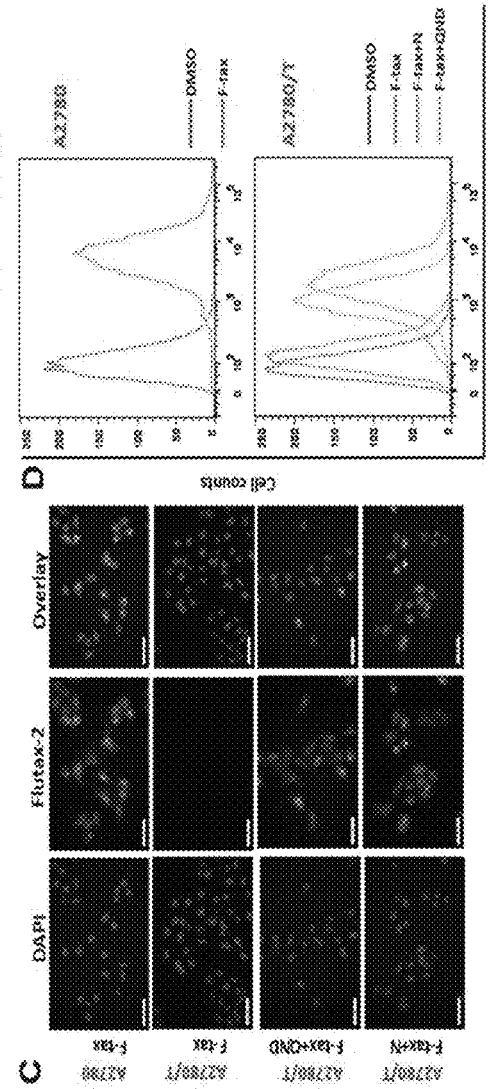

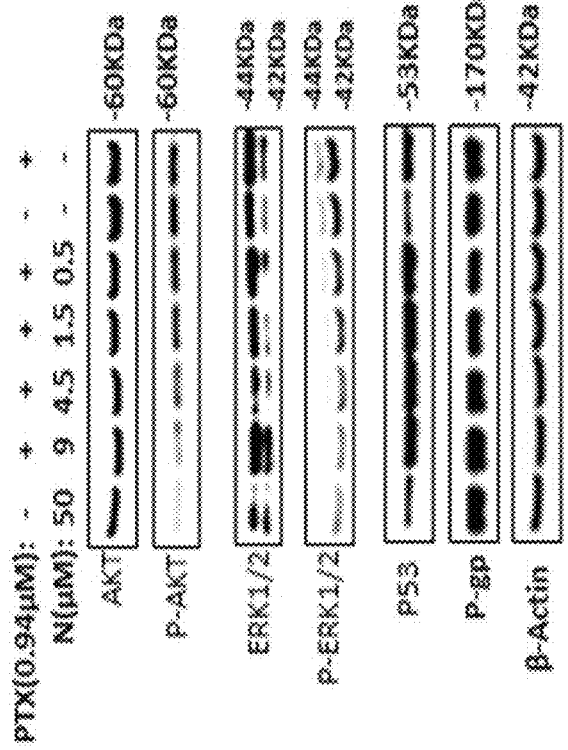
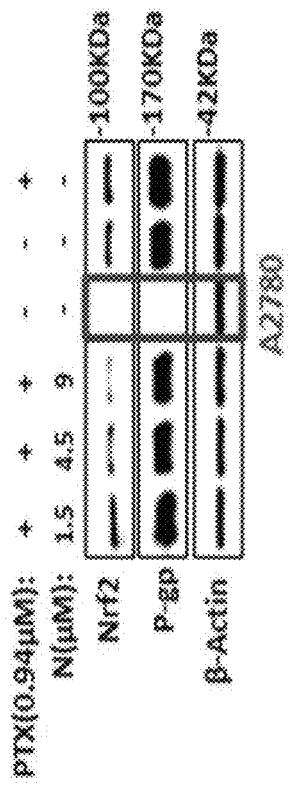
Fig. 8B
Fig. 8C

USE OF NOBILETIN IN CANCER TREATMENT

CROSS-REFERENCE TO RELATED APPLICATION

This application claims benefit under 35 U.S.C. §119(e) of U.S. Provisional application having Ser. No. 62/198,137 filed 29 Jul. 2015, which is hereby incorporated by reference herein in its entirety.

REFERENCE TO SEQUENCE LISTING

The hard copy of the sequence listing submitted herewith and the corresponding computer readable form are both incorporated herein by reference in their entireties.

FIELD OF INVENTION

This invention relates to a citrus methoxyflavone and the use thereof for treating cancer.

BACKGROUND OF INVENTION

Multidrug resistance (MDR) is a major reason for the clinical failure of many forms of chemotherapy. In the past few decades, a number of different mechanisms were found to mediate the development of MDR, and among which the most important were those associated with the overexpression of various ATP binding cassette (ABC) transport proteins. Permeability glycoprotein 1 (abbreviated as P-gp), also known as multidrug resistance protein 1 (MDR1) or ATP-binding cassette sub-family B member 1 (ABCB1), is the most extensively studied ABC transporter protein, which is significantly elevated in drug-resistant tumors and pumps out various anticancer drugs, such as taxanes, anthracyclines, vinca alkaloids, and epipodophyllotoxins. Since 1981, P-gp inhibitors have been intensively studied as potential MDR reversers. However, while several P-gp inhibitors were found among the available drugs, they have the disadvantage of toxicity and poor drug interaction profiles. Therefore, new and more effective compounds with low toxicity and fewer side effects are desirable.

SUMMARY OF INVENTION

In the light of the foregoing background, the present invention, in one aspect, is a pharmaceutical composition for treating multidrug resistance cancer, including a citrus methoxyflavone and a chemotherapeutic drug.

In an exemplary embodiment of the present invention, the citrus methoxyflavone can inhibit function of ABCB1 transporter such that intracellular accumulation of the chemotherapeutic drug is increased. In an exemplary embodiment of the present invention, the citrus methoxyflavone is nobiletin. In an exemplary embodiment, the chemotherapeutic drug is paclitaxel, docetaxel, doxombicin or daunorubicin. In another exemplary embodiment, the multidrug resistance cancer is paclitaxel-resistant cancer. In a further embodiment, the paclitaxel-resistant cancer is paclitaxel-resistant non-small cell lung cancer or paclitaxel-resistant ovarian cancer.

According to another aspect of the present invention, it provides a method of treating multidrug resistance cancer, including administrating a pharmaceutically effective amount of a citrus methoxyflavone and a chemotherapeutic drug to a subject in need thereof.

In an exemplary embodiment of the present invention, the citrus methoxyflavone can inhibit function of ABCB1 transporter such that intracellular accumulation of the chemotherapeutic drug is increased. In an exemplary embodiment of the present invention, the citrus methoxyflavone is nobiletin. In an exemplary embodiment, the chemotherapeutic drug is paclitaxel, docetaxel, doxombicin or daunorubicin. In another exemplary embodiment, the multidrug resistance cancer is paclitaxel-resistant cancer. In a further embodiment, the paclitaxel-resistant cancer is paclitaxel-resistant non-small cell lung cancer or paclitaxel-resistant ovarian cancer.

In a further aspect, the present invention is a method of enhancing the efficacy of a chemotherapeutic drug in treating multidrug resistance cancer, including (a) administering the chemotherapeutic drug to the subject; and (b) applying a citrus methoxyflavone.

In an exemplary embodiment of the present invention, the citrus methoxyflavone can inhibit function of ABCB1 transporter such that intracellular accumulation of the chemotherapeutic drug is increased. In an exemplary embodiment of the present invention, the citrus methoxyflavone is nobiletin. In an exemplary embodiment, the chemotherapeutic drug is selected paclitaxel, docetaxel, doxorubicin or daunorubicin. In another exemplary embodiment, the multidrug resistance cancer is paclitaxel-resistant cancer. In a further embodiment, the paclitaxel-resistant cancer is paclitaxel-resistant non-small cell lung cancer or paclitaxel-resistant ovarian cancer.

In a further aspect, the present invention is a method of sensitizing ABCB1-ovexpressing cells to chemotherapeutic drug in the treatment of multidrug resistance cancer, comprising the administration of nobiletin to a subject in need thereof.

In an exemplary embodiment of the present invention, the citrus methoxyflavone can inhibit function of ABCB1 transporter such that intracellular accumulation of the chemotherapeutic drug is increased. In an exemplary embodiment of the present invention, the citrus methoxyflavone is nobiletin. In an exemplary embodiment, the chemotherapeutic drug is selected paclitaxel, docetaxel, doxorubicin or daunorubicin. In another exemplary embodiment, the multidrug resistance cancer is paclitaxel-resistant cancer. In a further embodiment, the paclitaxel-resistant cancer is paclitaxel-resistant non-small cell lung cancer or paclitaxel-resistant ovarian cancer.

BRIEF DESCRIPTION OF FIGURES

The patent or application file contains at least one drawing executed in color. Copies of this patent or patent application publication with color drawing(s) will be provided by the Office upon request and payment of the necessary fee.

FIGS. 2A to 2F demonstrates multidrug resistance in paclitaxel (PTX)—resistant ovarian cancer cells (A2780/T) and the parental sensitive cells (A2780). The cells were treated with various concentrations of PTX (FIG. 2A) and doxorubicin (DOX) (FIG. 2B) for 48 hours. Cell growth was determined using the Sulforhodamine B (SRB) assay. The expressions of ABCB1 transporter in A2780 and A2780/T cells were analyzed at level of both MDR1 mRNA by RT-qPCR (FIG. 2C) and P-gp protein level by Western blotting (FIG. 2D). (##: Significantly different from A2780 cells with P<0.01). Protein expression levels after normalized relatively to that of β-actin. Cytotoxicity of nobiletin alone in pairs of A2780/T or A2780 cells was analyzed (FIG.

Figure 2F:
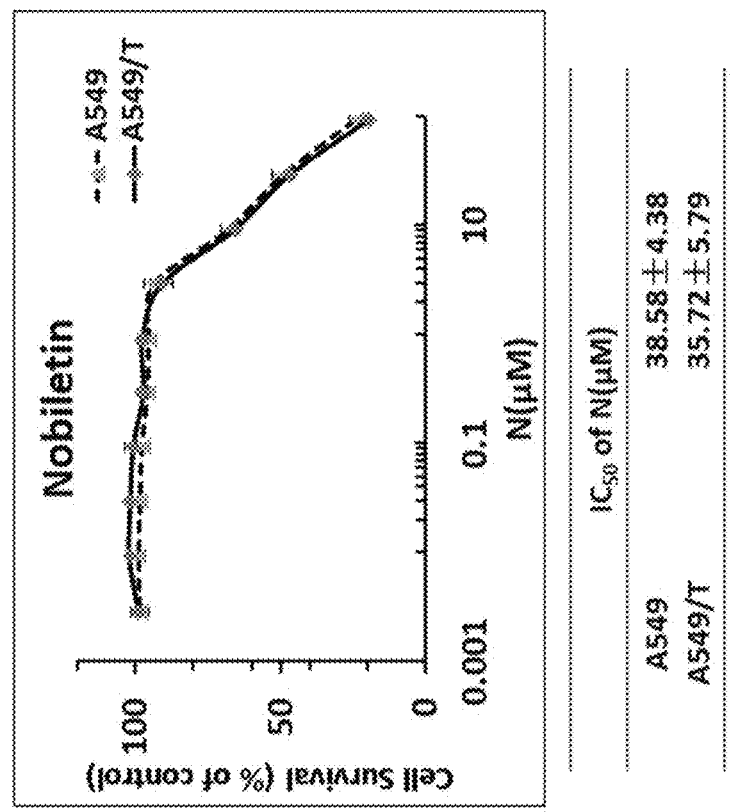

2E). Cytotoxicity of nobiletin alone in pairs of A549 or A549/T cells was analyzed (FIG. 2F).

Figures 3D, 3E:
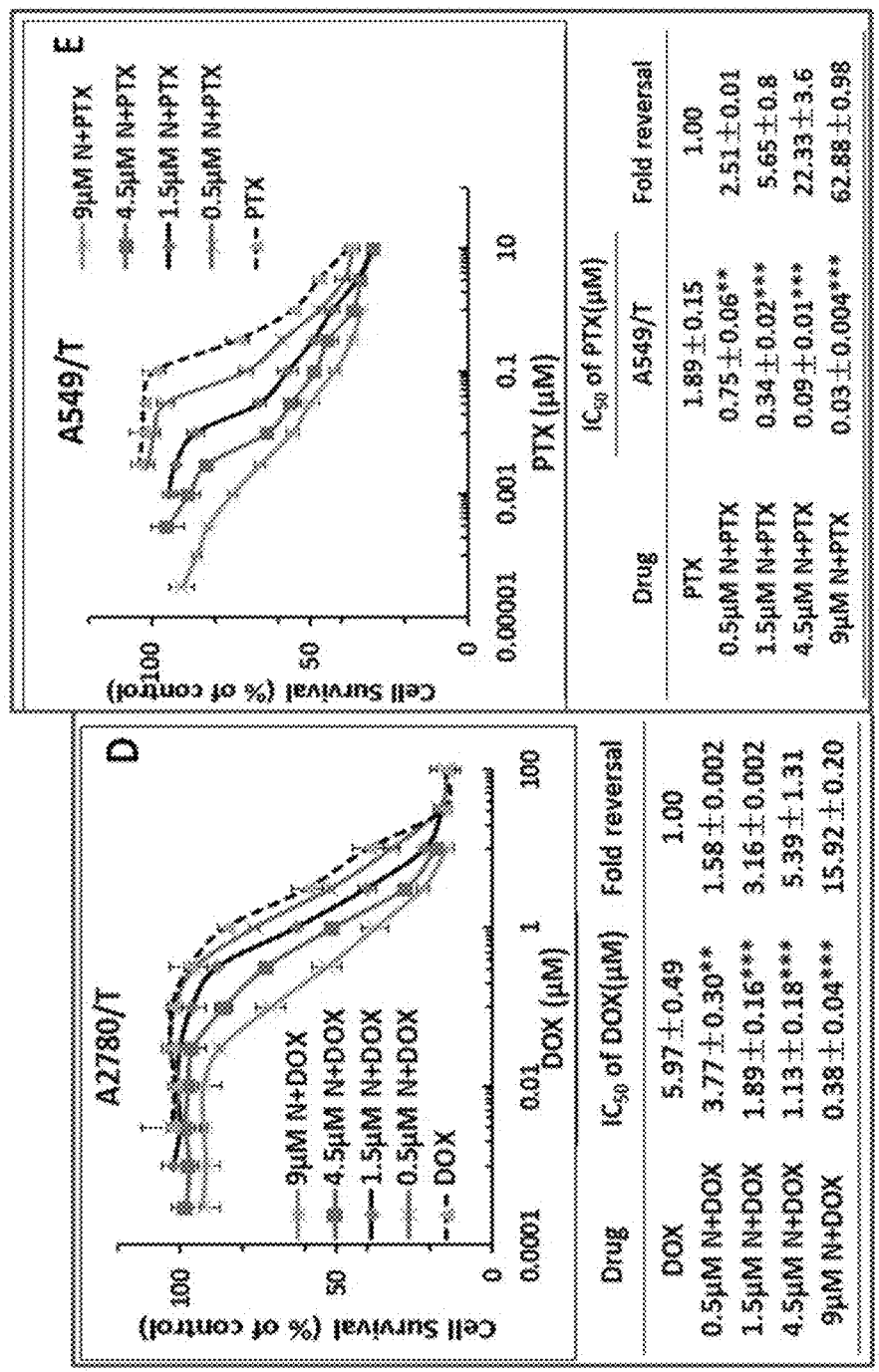
Figures 3F, 3G:
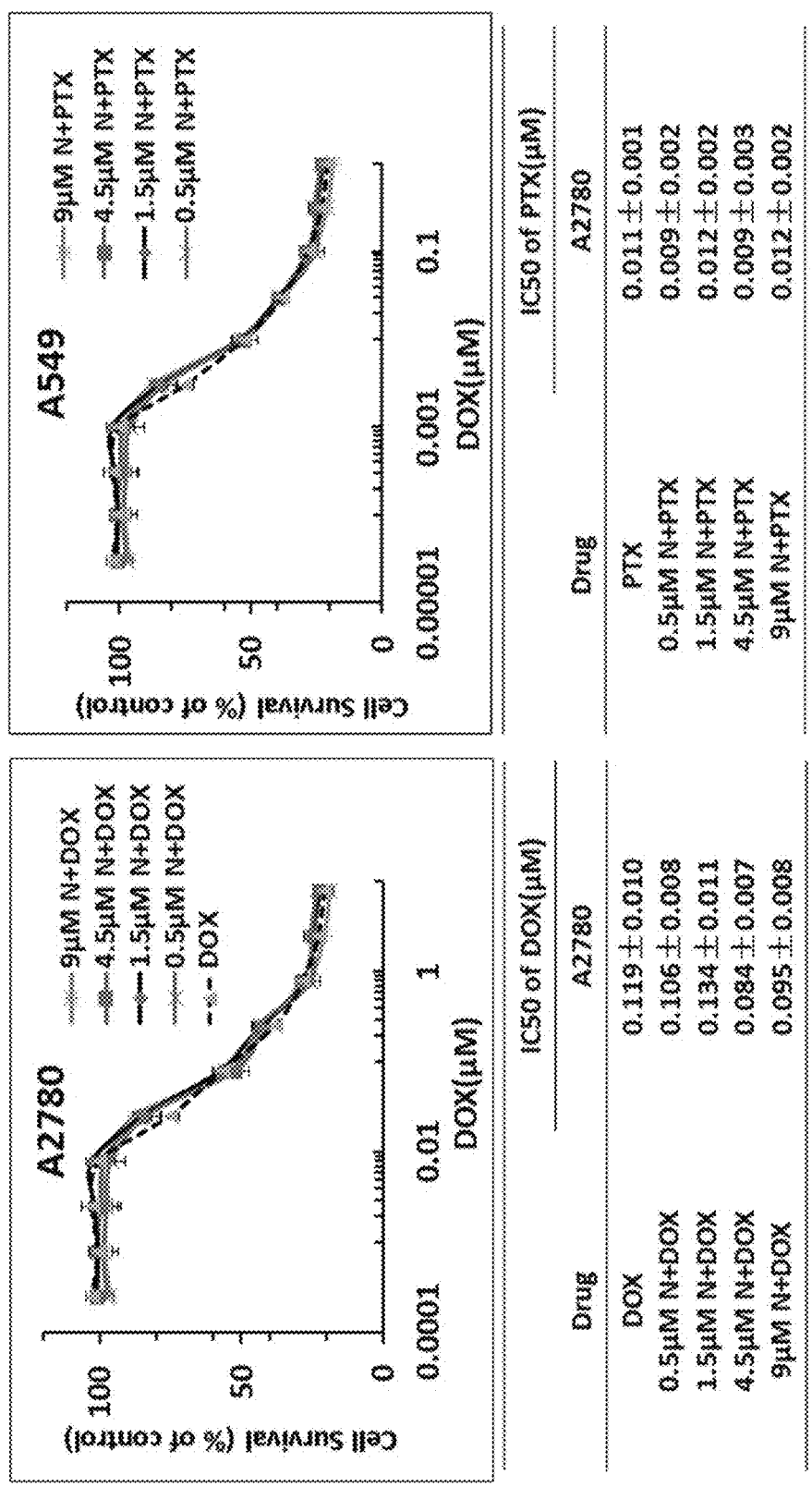

FIGS. 3A to 3G show the effect of nobiletin on reversing ABCB1-mediated resistance. Cells were treated with the indicated drugs for 48 hours and subjected to SRB assay. Nobiletin reduces the $IC_{50}$ of paclitaxel in resistant cancer cells (A2780/T) (FIG. 3B) but not in drug sensitive cells (A2780) (FIG. 3A). The cells were treated with paclitaxel in the presence or absence of nobiletin for 12 days. Colony numbers were counted after Giemsa staining using the software of Quantity one-Colony counting (FIG. 3C). Nobiletin reduces the $IC_{50}$ of doxorubicin in resistant cancer cells (A2780/T) (FIG. 3D). Nobiletin reduces the $IC_{50}$ of paclitaxel in paclitaxel-resistant human non-small cell lung cancer (NSCLC) cancer cells (A549/T). Nobiletin does not affect the $IC_{50}$ of doxorubicin in sensitive cancer cells (A2780) (FIG. 3F). Nobiletin does not affect the $IC_{50}$ of paclitaxel in paclitaxel-sensitive human non-small cell lung cancer (NSCLC) cancer cells (A549) (FIG. 3G). $IC_{50}$ values are represented as mean±SD of three independent experiments performed in triplicate. ## or , P<0.01, ### or *, P<0.001, significantly different from those obtained in the absence of nobiletin.

Figures 4A, 4B:
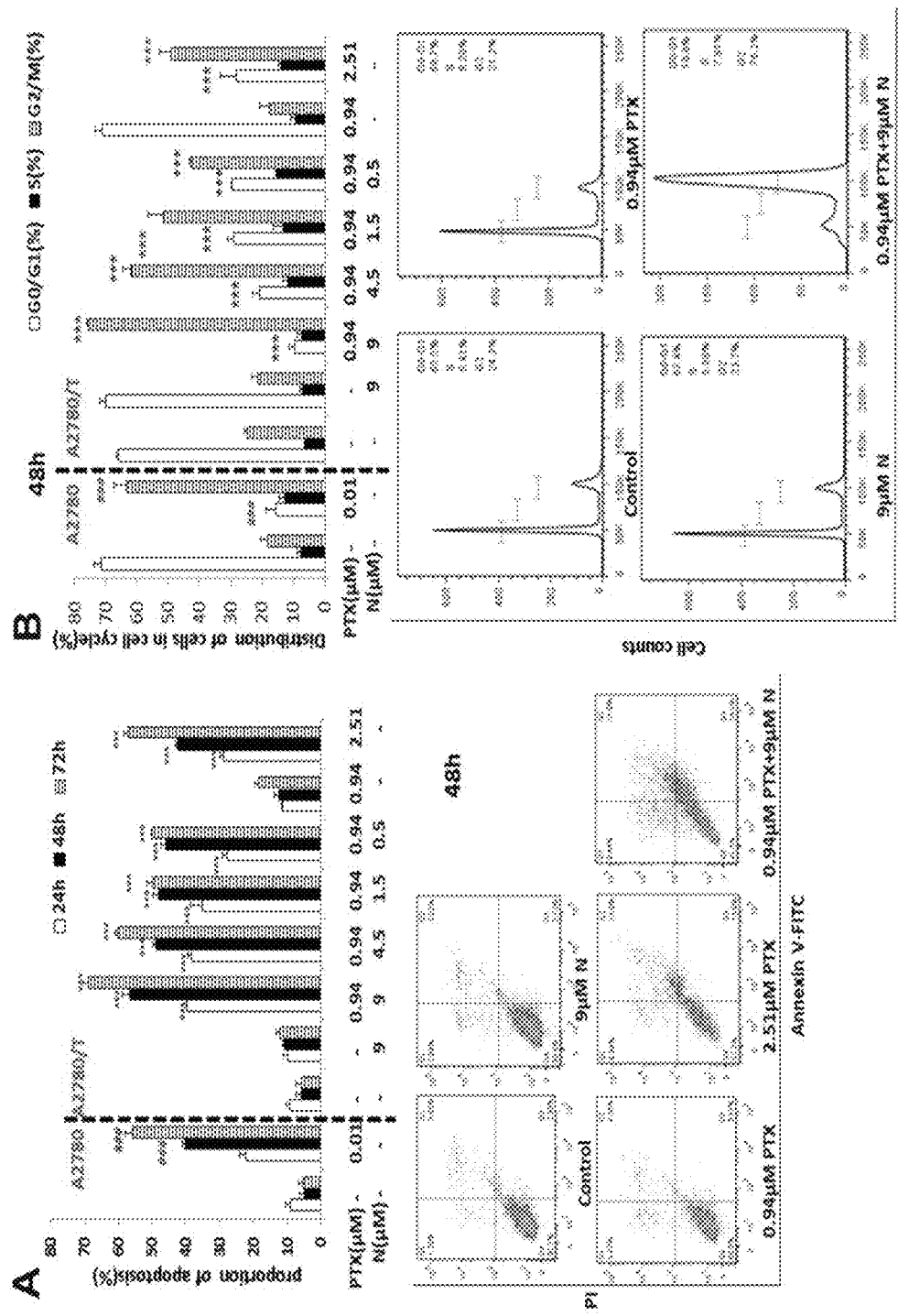
Figure 6A:
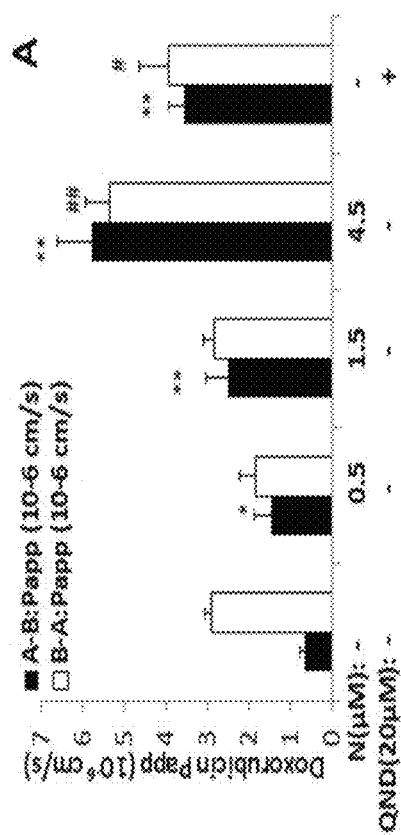
Figure 6B:
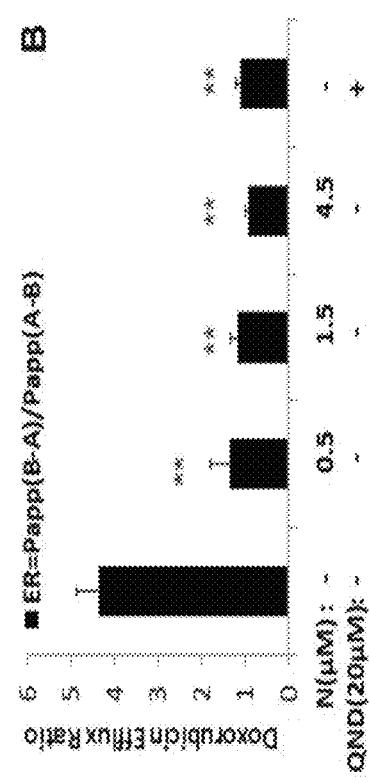
Figure 7A:
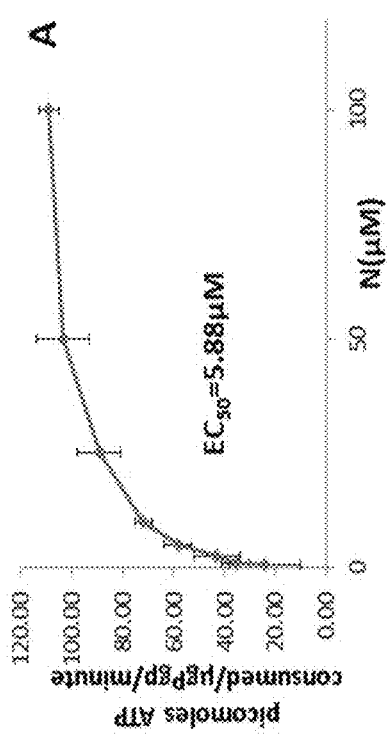
Figure 7B:
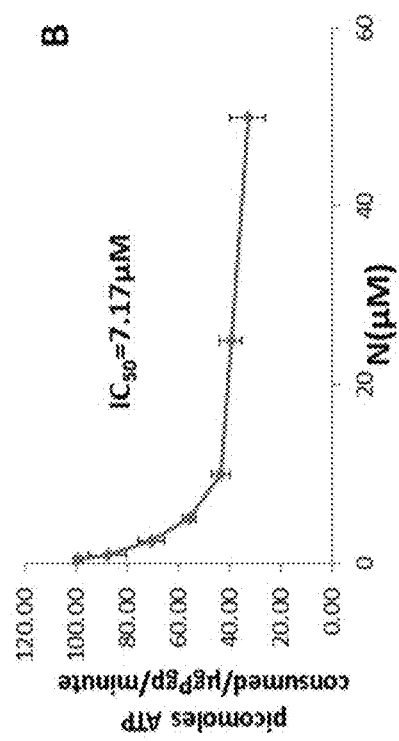

FIGS. 4A and 4B show the effect of nobiletin on the apoptosis and cell cycle of MDR cancer cells induced by PTX. Effect of nobiletin on the percentage of annexin V-FITC-positive staining in A2780/T cells treated with 0.94 µM PTX using flow cytometry (FIG. 4A). Effect of nobiletin on DNA-ploidy flow cytometric analysis of A2780/T cells treated with 0.94 µM PTX (FIG. 4B). Different concentrations of nobiletin were added to A2780/T cells with PTX for 48 h. The data is representative of three different experiments and are shown as mean±SD (n=3). ## or , P<0.01, ### or *, P<0.001, significantly different from those obtained in the absence of nobiletin FIGS. 5A to 5D show the effect of nobiletin on intracellular accumulation of doxorubicin (DOX) and flutax-2 (F-tax, a fluorescent taxol derivative) in drug-resistant ovarian cancer cells. A2780 cells or A2780/T Cells treated with 5 µM DOX (with results shown in FIGS. 5A and 5B) or 5 µM F-tax (with results shown in FIGS. 5C and 5D) for 8 hours in the absence or presence of 4.5 µM nobiletin, and 20 µM quinidine (positive control) as indicated. Intracellular DOX and F-tax accumulation were observed with a florescence microscope (with results shown in FIGS. 5A and 5C) and evaluated by measuring florescence with flow cytometry (with results shown in FIGS. 5B and 5D) as described below, for example Section 2.6. The experiments were repeated for at least 3 times, presented are representative images FIGS. 6A and 6B show that nobiletin increases the adsorption and inhibits the efflux ratio of DOX in Caco-2 cells. FIG. 6A shows the effect of nobiletin on the directional transport of DOX (10 µM) across Caco-2 cell monolayers, whereas FIG. 6B illustrates the effects of nobiletin on the efflux ratio of DOX (10 µM) in Caco-2 cell monolayers. Data represents the mean±SD of three individual determinations. ☐ AP→BL transport, ■ BL→AP transport. ## or , P<0.01, ### or *, P<0.001, significantly different from those obtained in the absence of nobiletin FIGS. 7A and 7B show that nobiletin was tested at a range of concentrations for its capacity to stimulate P-gp ATPase activity and to inhibit 200 µM verapamil-stimulated P-gp ATPase activity. $EC_{50}$ measurements for stimulating P-gp ATPase activity by nobiletin were shown in FIG. 7A, whereas $IC_{50}$ measurements for inhibiting 200 µM verapamil-stimulated P-gp ATPase activity by nobiletin were shown in FIG. 7B. Luminescence was read on a luminometer and data was analyzed as described below, for example Section 2.9

Figure 8A:
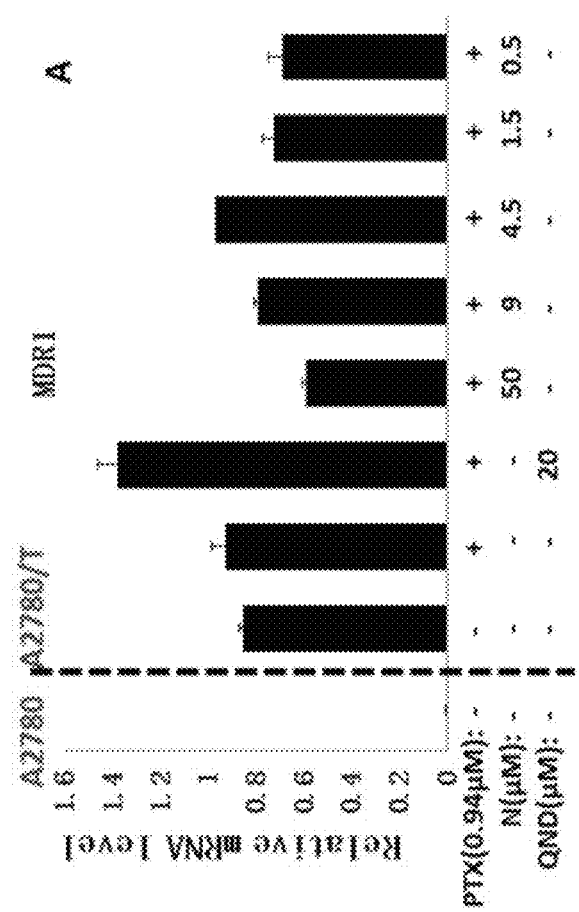
Figure 9A:
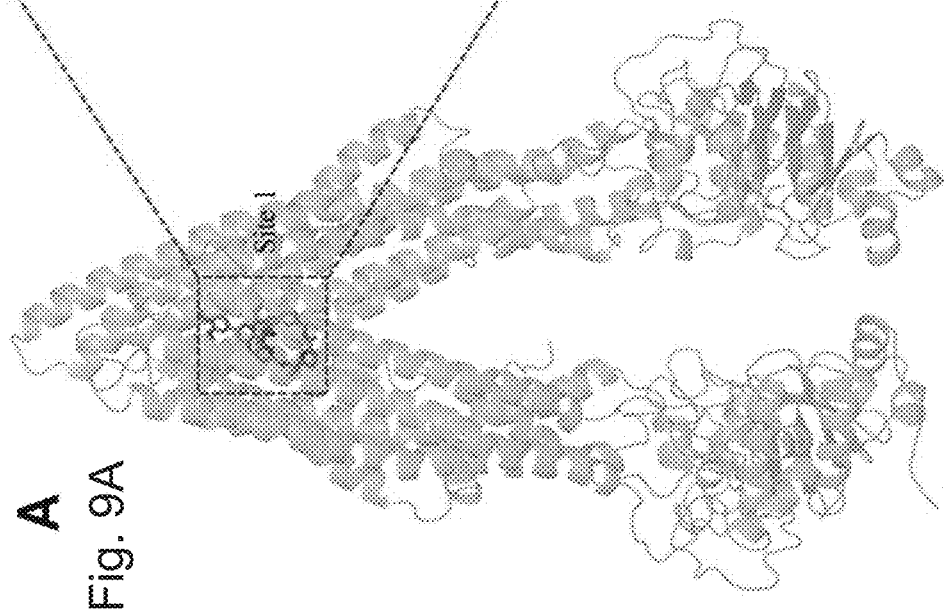
Figure 9B:
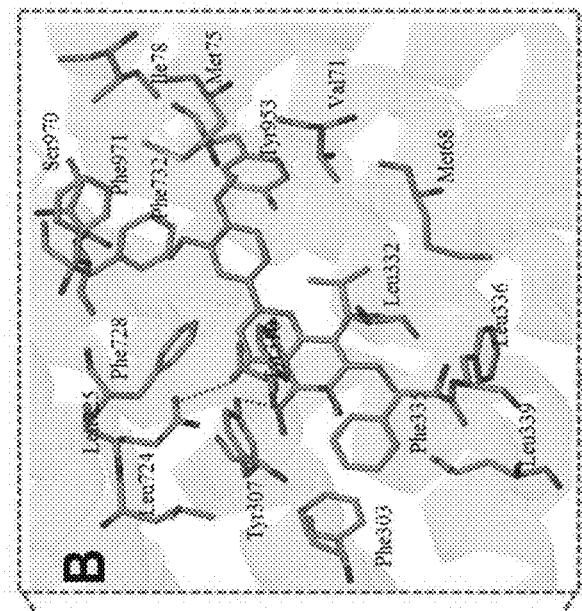
Figure 9C:
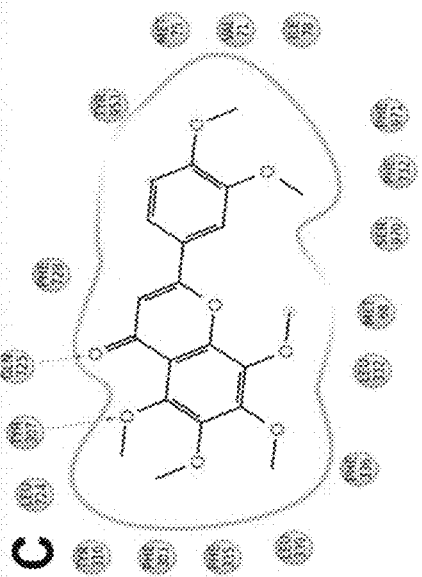

FIGS. 8A to 8C show the effects of the combinational treatment of paclitaxel and nobiletin on ABCB1 expression and AKT/ERK/Nrf2 pathway in ABCB1 overexpressing ovarian cancer cells. A2780/T cells or A2780 cells were treated with nobiletin at various concentrations for 48 hours. (FIG. 8A) The MDR1 mRNA level was determined by RT-PCR. Equal amounts of total lysate were loaded and detected by Western blot as shown in FIGS. 8B and 8C. Combination treatment of paclitaxel and nobiletin did not influence either MDR1 mRNA or P-gp expression levels, but unregulated the p53 expression and reduced the Nrf2 as well as the phosphorylation of AKT/ERK. The experiments were performed three times FIGS. 9A to 9C illustrate the docking analysis of nobiletin with human ABCB1 homology model. FIG. 9A shows the cartoon style of the homology model of human ABCB1 in which the binding poses of QZ59-RRR (PDB: 4M2S) (green) and nobiletin (orange) are shown in site 1. FIG. 9B shows the interactions between nobiletin and the surrounding residues. The red dotted line represents hydrogen bond between atoms. FIG. 9C shows a two dimensional interaction sketch between nobiletin and its binding site residues of human ABCB1. Residues are shown as colored bubbles, cyan indicates polar and green indicates hydrophobic residues.

Figures 10A, 10B:
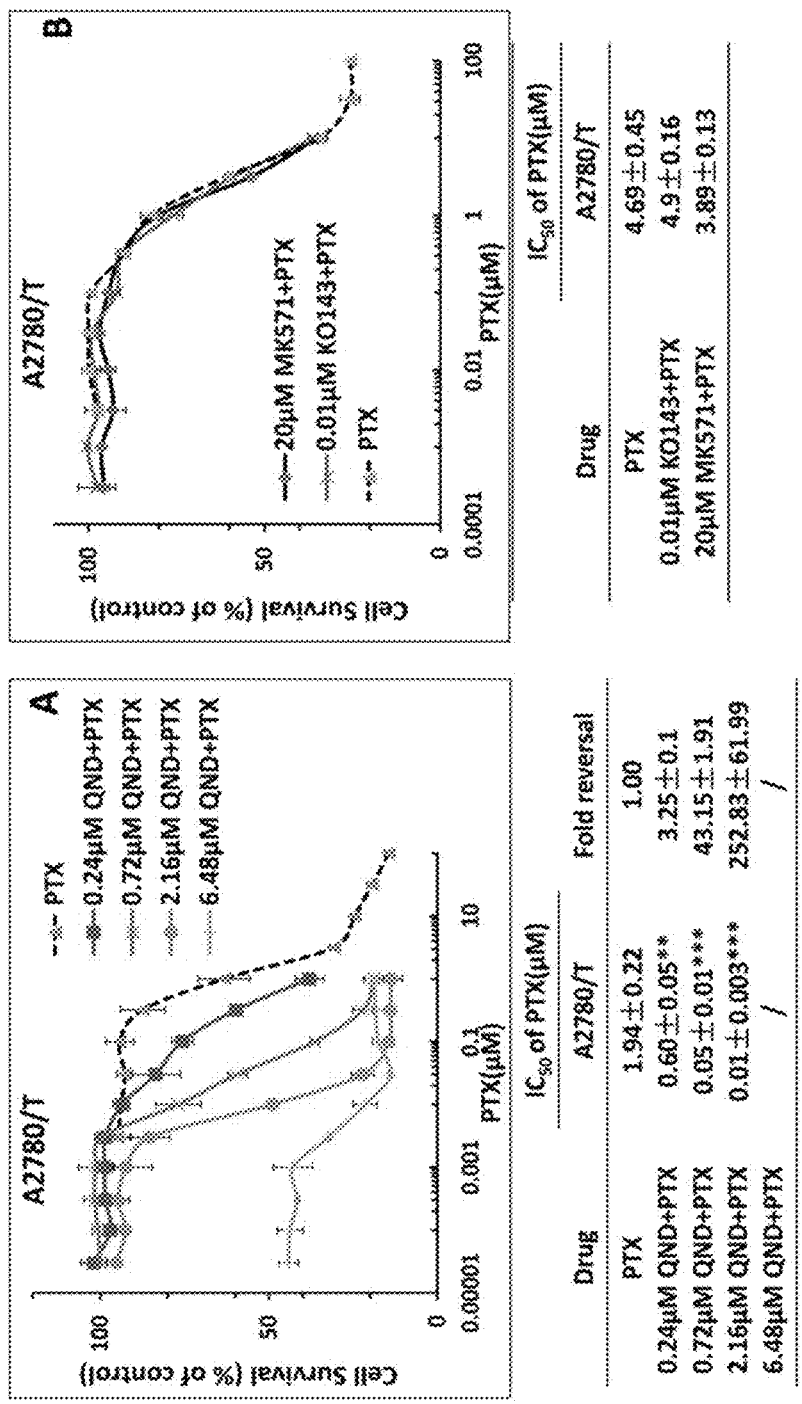

FIGS. 10A and 10B show the effect of transporter inhibitor on the paclitaxel sensitivity of resistant cells. Quinidine (MDR1 inhibitor) (FIG. 10A) but not MK571 (MRPs inhibitor) or KO143 (BCRP inhibitor) (FIG. 10B) reduces the $IC_{50}$ of paclitaxel in resistant cancer cells (A2780/T). Cells were treated with the indicated drugs for 48 hours and subjected to SRB assay. , P<0.01, *, P<0.001, Student's t-test (n=3) or one-way ANOVA (n=3).

FIGS. 11A to 11D show the inhibition effect of nobiletin on the directional transport and the efflux ratio of Rho123 (10 µM) (FIGS. 11A and 11B) or Flutax-2 (FIGS. 11C and 11D) across Caco-2 cell monolayers. Data represent the mean±SD of three individual determinations. ☐ AP→BL transport, ■BL→AP transport. ## or , P<0.01, Milt or *, P<0.001, significantly different from those obtained in the absence of nobiletin.

Figure 12A:
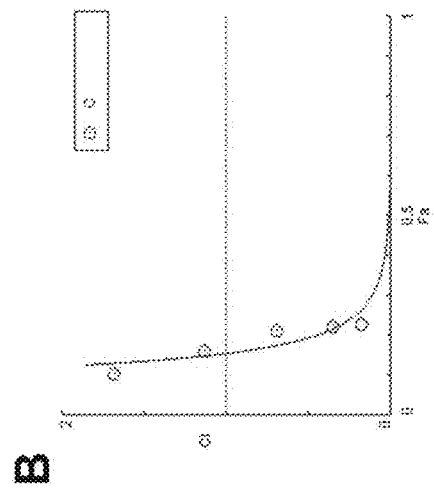
Figure 12B:
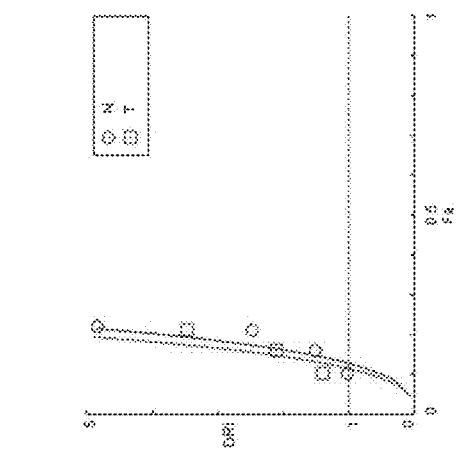
Figure 12C:
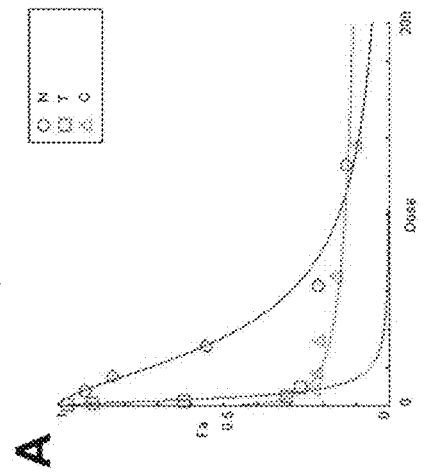
Figure 12D:
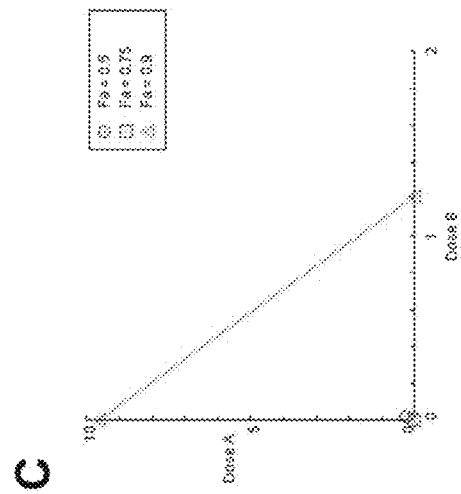

FIGS. 12A to 12D show the quantitative diagnostic graphics for the synergistic effect between nobiletin (N) and paclitaxel (T) generated by the computer simulation. FIG. 12A shows the fraction affected (Fa)-Dose plot for nobiletin (N), paclitaxel (T) and combination (C). FIG. 12B shows the Fa-CI plot (Chou-Talalay plot). FIG. 12C shows the classic isobologram whereas FIG. 12D shows the Fa-DRI plot (Chou-Martin plot) for the constant ratio combination design. CI (combination index)<1 represents synergism; CI=1 indicates additive effect, and CI>1 represents antagonism. DRI>1 represents reduced dose and reduced toxicity.

Figure 13:
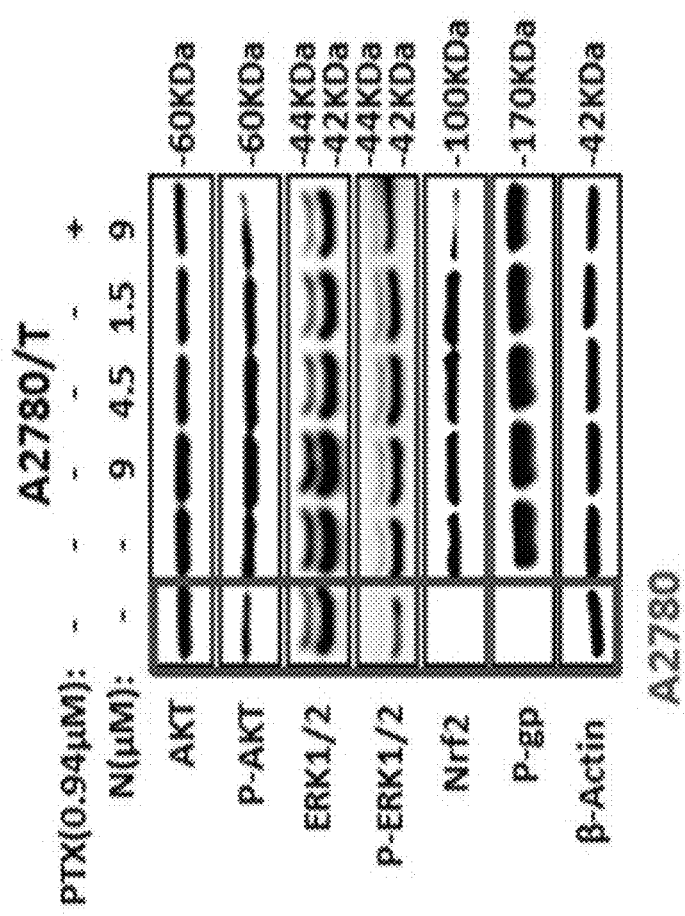

FIG. 13 shows the effects of nobiletin alone on ABCB1 expression and AKT/ERK/Nrf2 pathway in ABCB1 overexpressing ovarian cancer cells. A2780/T cells or A2780 cells were treated with nobiletin at various concentrations for 48 hours. Equal amounts of total lysate were loaded and detected by Western blot. Nobiletin alone did not influence ABCB1, Nrf2, total and phosphorylation of AKT/ERK expression levels. The experiments were performed three times.

DETAILED DESCRIPTION OF THE PREFERRED EMBODIMENTS

As used herein and in the claims, "comprising" means including the following elements but not excluding others.

Recently studies showed that up-regulation of PI3K/AKT, ERK and Nrf2 pathways are associated with resistance to multiple chemotherapeutic drugs. Antitumor drugs are known to inhibit these signaling pathways and consequently induce tumor cell sensitive to chemotherapy drugs. Therefore, identification of the inhibitors that potently inhibit the activation of AKT/ERK and Nrf2-denpendent response is desired to develop inhibiters to treat chemoresistant cancer. Preferably the desired MDR reverser is safe and non-toxic.

Figure 1:
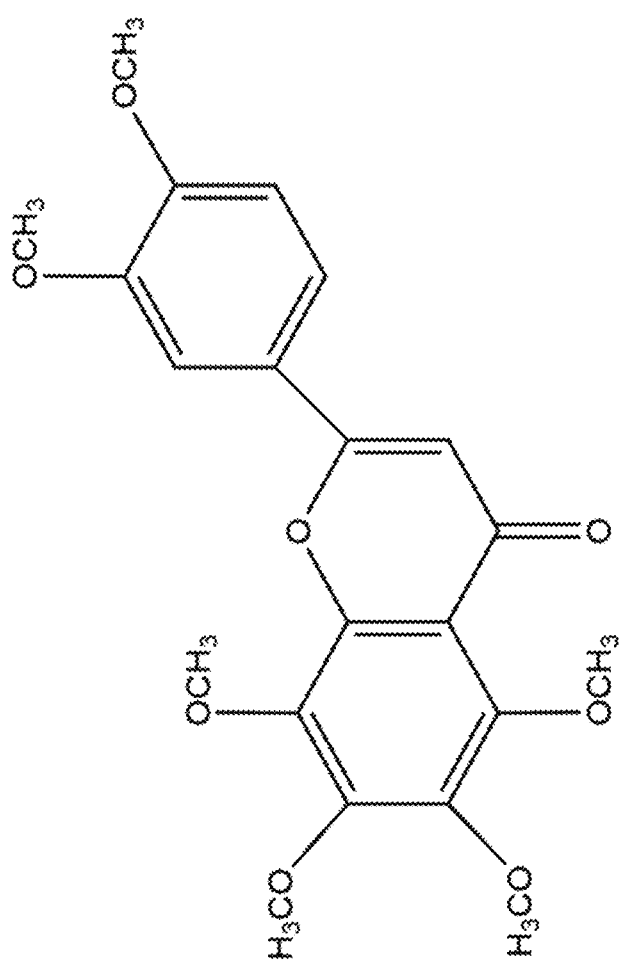
FIG. 1 is the chemical structure of nobiletin.

Nobiletin, the structure of which is shown in FIG. 1, is a non-toxic dietary polymethoxylated flavone and presents in some citrus fruits such as *Citrus depressa* (shiikuwasa) and *Citrus sinensis* (oranges). It was reported to exhibit multiple biological effects such as anti-inflammatory, anti-tumor, and neuroprotective properties. As a potent chemo-preventive agent, nobiletin inhibited the growth of several prostate cancer cell lines with $IC_{50}$ values around 100 μM by significantly increasing $G_0/G_1$ phase arrest. Moreover, it was found that nobiletin (20 μM) could increase the uptake of [$^3$H] vinblastine in Caco-2 cells and in ABCB1 transfected cell line LLC-GA5-COL300 by 3- and 1.8-fold, respectively, indicating the potential P-gp inhibition effect of nobiletin.

The inventors performed a series of experiments to investigate the reversal effect of nobiletin on ABCB1 overexpression cancer cell lines to chemotherapeutic agents. Nobiletin at achievable nontoxic plasma concentrations (0.5 to 9 μM) significantly inhibits the ABCB1 overexpressing MDR cancer cell lines by inhibiting the AKT/ERK/Nrf2 pathways and modulating the ABCB1 function, and has the potential for use in combination therapies to treat MDR.

1. Materials and Methods 1.1 Reagents and Cell Culture

Nobiletin was purchased from Dalian Meilun Biology Technology Co., Ltd, and the structure and purity was confirmed by LC-MS in our lab. Flutax-2 was purchased from Life Technologies. Paclitaxel (PTX) and doxorubicin (DOX), verapamil (Vrp), quinidine (QND), 5-fluorouracil, docetaxel, dounorubicin and other chemicals were purchased from Sigma-Aldrich (St. Louis, Mo.). Stock solutions of nobiletin (40 mM), DOX (40 mM) and PTX (80 mM) were prepared in dimethyl sulfoxide (DMSO) and appropriate working concentrations were prepared in cell culture medium immediately before use. The Roswell Park Memorial Institute (RPMI) 1640 medium, fetal bovine serum, penicillin and streptomycin were obtained from Life Technologies Inc. (Grand Island, N.Y.). The DMSO, RNase A, leupeptin, aprotinin, phenyl methyl sulfonyl fluoride, Triton X-100 and propidium iodide (PI) were purchased from Sigma-Aldrich Co. (St Louis, Mo.). ERK 1/2 and actin antibodies were purchased from Santa Cruz Biotechnology, USA; P-gp and P53 antibodies were purchased from Calbiochem and Abcam; other antibodies such as AKT, P-AKT, and P-ERK1/2 were purchased from Cell Signaling Technology, Inc.

Human ovarian cancer cells A2780 and its PTX-resistant cell line A2780/T, human non-small cell lung cancer (NSCLC) A549 and its PTX-resistant cell line A549/T were generously provided by Professor Zhi-Hong Jiang (Macau University of science and technology, Macau). Cells were grown as monolayers in RPMI-1640 medium supplemented with 10% fetal bovine serum (GIBCO, Paisley, Scotland) at 37° C. in a humidified 5% $CO_2$ atmosphere. The indicated concentration of paclitaxel (0.94 μM) was added to the culture medium to maintain drug resistance for A2780/T and A549/T. The mRNA level of P-gp didn't changed significantly after grown in drug-free culture medium for 10 days for both resistant cell lines. The human colon carcinoma cell line Caco-2 was purchased from the ATCC, and cells at passage numbers 25-35 were used for the assays.

1.2 Cell Cytotoxicity Assay

Sulphorhodamine B (SRB) assays were used for cell density determination, based on sensitive measure of total cellular protein, which perform similarly compared with other proliferation assays such as MTT assay. Briefly, cells were seeded into flat bottomed 96-well plates at an initial density of $7.5 \times 10^3$ per well before treatment. Cells were exposed to varying concentrations of nobiletin (9, 4.5, 1.5 and 0.5 μM) and combined them with varying concentrations of PTX (1 μM to 0.03 nM with 3.16 fold diluted, 10 μM to 0.3 nM with 3.16 fold diluted, 100 μM to 3 nM with 3.16 fold diluted respectively) to test whether this combination can enhance the growth inhibition of MDR cancer cells. After removing the medium, cells were fixed in 10% trichloroacetic acid for 1 h at 4° C. and then washed with water five times. 0.4% SRB dissolved in 1% v/v acetic acid was added and incubated 30 mm for staining. The cells were quickly washed with 1% acetic acid and left to dry overnight. The protein bound SRB was solubilized by adding 200 μl 10 mM Tris buffer per well and was measured at wavelengths 490 nm using a plate reader (Spectra MAX 250; Molecular Devices, Sunnyvale, Calif.). The optical density of SRB in each well is directly proportional to the cell number. The degree of resistance was estimated by comparing the $IC_{50}$ (concentration of 50% inhibition) for the MDR cells to that of parent sensitive cells, while, the degree of reversal of MDR was calculated by dividing the $IC_{50}$ for cells with the chemotherapeutic drugs in the absence of nobiletin by that obtained in the presence of nobiletin.

1.3 Colony Formation Assay

For the colony formation assays, A2780/T or A549/T cells (200 cells/well) in 6-well plates were treated with culture medium (containing 0.94 μM PTX) or with nobiletin in different concentrations (containing 0.94 μM PTX) for 12 days. The A2780/T cells were trypsinized and plated in fresh culture medium at a density of 600 cells/9.6 cm$^2$ plate. Subsequently, the cells were fixed with 70% ethanol and stained with crystal violet (0.5% in ethanol). The plates were rinsed with phosphate buffered saline (PBS), and the colony numbers were counted using the software of Quantity one-Colony counting.

1.4 Cell Cycle Analysis

A2780/T cells were harvested 24 hours, 48 hours, or 72 hours after treatment and washed twice with ice-cold PBS. The cells were fixed and permeabilized with 70% ice-cold ethanol overnight at 4° C. or 2 h at −20° C. After one additional wash in PBS, cells were stained with a staining solution containing propidium iodide (PI) (50 μl/ml) and RNase A (250 μg/ml) for 30 min at room temperature. They were then pelleted, washed and suspended in PBS to a final concentration of $1 \times 10^6$/ml and analyzed by flow cytometry BD FACS Aria (BD Biosciences, San Jose, Calif.).

1.5 Apoptosis Analysis by Annexin-V/PI Double-Staining Assay

After treatment, $1 \times 10^6$ cells were collected, washed and suspended in 100 μl of binding buffer (10 mM N-2-hydroxyethylpiperazine-N,-2-ethanesulfonic acid/NaOH, 140 mM NaCl, 2.5 mM CaCl2, pH 7.4). Apoptotic cells were identified by double supravital staining with 5 μl recombinant FITC (fluorescein isothiocyanate)-conjugated Annexin-V and 5 μl PI (50 μg/ml). The cells were stained for 15 mM at room temperature in the dark, and analyzed by fluorescenceactivated cell sorting cater-plus flow cytometry. Data acquisition and analysis were performed in BD FACS Aria with FlowJo software.

1.6 Combination Index in Nobiletin Combination Studies

The synergistic therapeutic effect for the combination of nobiletin and PTX was evaluated using the Chou-Talalay Method. "Combination index" (CI) was calculated by this method to quantitatively depict synergism (CI<D, additive (CI=1), or antagonism (CI>1) effect. Briefly, drug resistant A2780/T cells were exposed to a serially diluted mixture of nobiletin ($IC_{50}$ 31.62 μM) and PTX ($IC_{50=2.51}$ μM) for 48 hours. The 2-fold serial dilution with several concentration points above and below its $IC_{50}$ value was used for evaluating cytotoxicity of combination by SRB method as above description. With the use of CalcuSyn software v. 2.1 (Bio-soft), synergy is further refined as synergism (combination index=0.3-0.7), strong synergism (combination index=0.1-0.3), and very strong synergism (combination index <0.1).

1.7 Intracellular Accumulation of Doxorubicin and Flutax-2

1.7.1 Fluorescence Microscopy Observation

A2780 or A2780/T cells ($5 \times 10^6$) were cultured on the cover glass (ISO LAB 20×20 mm). DOX (5 μM), or flutax-2 (1 μM) (active fluorescent taxoids) alone or in combination with nobiletin (4.5 μM) was added and incubated for 8 h. After treatment, cells were fixed in 4 wt % formaldehyde (Sigma-Aldrich). Nuclear DNA was stained with 1 μg/mL blue-fluorescent DAPI (1 mg/mL in $H_2O$ stock solution; Invitrogen D1306). One drop of fluorescent preservation solution (fluorsave reagent, CALBIOCHEM) was added before observation. Imaging was carried out for comparing the intracellular accumulation of DOX and flutax-2 with a Fluorescence Microscopy (Leica DM2500, Leica, Germany).

1.7.2 Flow Cytometry Analysis

Flutax-2 (1 μM) and DOX (5 μM) was added to A2780 or A2780/T cells and incubated with or without nobiletin (4.5 μM) for 8 h. Cells were detached, re-suspended in 500 μl of PBS after washed twice with cold PBS, and analyzed by flow cytometry (BD FACS Aria, BD Biosciences, San Jose, Calif.). Excitation and emission wavelengths (nm) used for DOX and flutax-2 were as follows: 480 to 585; and 496 to 524. Quinidine (QND, 20 μM), a known ABCB1 inhibitor, was used as a positive control.

1.8 Transport Assay in Caco-2 Monolayer Model

The Caco-2 cell line was seeded on Millipore Millicell plates and formed a confluent monolayer over 21 days prior to the experiment. The integrity of the cell monolayers was checked by measuring the transepithelial electrical resistance (TEER) before and after the transport experiments using a WPI EVOM2 Epithelial voltohmmeter fitted with STX2 chopstick electrodes (World Precision Instruments, Sarasota, Fla., USA). On day 21, the transport assay included apical-to-basolateral (A→B) and basolateral-to-apical (B→A) transport rate determinations for rhodamin123 (5 μM), flutax-2 (1 μM) and DOX (10 μM) in Caco-2 cell line was carried out over a 2 hour time period. Briefly, samples (100 μL) were collected from apical/basolateral side of Caco-2 cell monolayer at predetermined times of 30, 60, 90, and 120 min, and immediately detected for the fluorescence intensity in 96 well black plate (Corning; Cat. 3603) using a microplate reader (infinite M200 PRO, TECAN, Switzerland). For inhibition studies, bidirectional transport of target compound was conducted in Caco2 cell monolayer with nobiletin added in both apical and basolateral chambers. Quinidine (QND) was used as potent control inhibitors of P-gp.

The apparent permeability coefficients (Papp) were calculated as $$P_{app} = \frac{dQ}{dt} \times \frac{1}{C0A}$$

Where dQ/dt (mM/sec) is the rate of permeation of compound across the cells, $C_0$ (mM) is the donor compartment concentration at time zero and A ($cm^2$) is the area of the cell monolayer. The decrease in Efflux Ratio (ER=Papp (B to A)/Papp (A to B)) in the presence of nobiletin and putative inhibitor QND was determined to assess their relative inhibitory potency to transporter P-gp.

1.9 ABCB1 ATPase Activity Assay

The impact of nobiletin on P-gp ATPase activity was estimated by PgpGlo™ assay systems (Promega, USA). The inhibitory effects of nobiletin were examined against a verapamil-stimulated ABCB1 ATPase activity. Sodium orthovanadate ($Na_3VO_4$) was used as an ABCB1 ATPase inhibitor. Following manufacture's instruction, 0.25 mM $Na_3VO_4$, 0.5 mM verapamil, or nobiletin in various concentrations were incubated with assay buffer, 25 μg recombinant human ABCB1 membranes and 5 mM MgATP at 37° C. for 40 min. For examination the inhibitory effects of nobiletin against verapamil-stimulated P-gp ATPase activity, then 200 μM verapamil was added with nobiletin together. Luminescence was initiated by ATP detection buffer. The plate (white opaque 96-well, corning, USA) was further incubated at room temperature for 20 mM to develop luminescent signal, and was read with luminometer (infinite M200 PRO, TECAN, Switzerland). The changes of relative light units (ARLU) were determined by comparing $Na_3VO_4$-treated samples with nobiletin only or nobiletin and verapamil combination-treated samples, and hence, the ATP consumed was calculated by comparing to a standard curve.

1.10 RT-PCR Analysis

RT-PCR was performed to evaluate MDR1 mRNA expression. mRNA from cell lysates were purified by binding to poly(dT) magnetic beads (Life technologies) and reverse transcribed by using SuperScript II (Life technologies). Standard quantitative RT-PCR was performed in duplicates at least two to three times by using SYBR Green (Molecular Probes) protocols on the ViiA™ 7 Real-Time PCR System (Life technologies). The primer sequences: 5'-GAGAGATCCTCACCAAGCGG-3' (SEQ ID NO:1) and 3'-CGAGCCTGGTAGTCAATGCT-5' (SEQ ID NO:2) for MDR1, and 5'-AGAAGGCTGGGGCTCATTTG-3' (SEQ ID NO:3) and 3'-AGGGGCCATC-CACAGTCTTC-5' (SEQ ID NO:4) for control gene eukaryotic translation initiation factor (TIF). RT-PCR data were normalized by measuring average cycle threshold (Ct) ratios between candidate genes and control gene TIF.

1.11 Western Blot Analysis

The total cellular samples were harvested and rinsed twice with ice-cold PBS buffer. Cell extracts were lysed in RIPA buffer (50 mM Tris (pH 7.4), 150 mM NaCl, 1% Triton X-100, 1% sodium deoxycholate, 0.1% SDS, sodium orthovanadate, sodium fluoride and EDTA) containing protease inhibitor cocktails (Roche Life Science, USA). Protein concentration was determined using the BCA protein assay kit. Equal amounts of cell lysates were resolved by SDS-PAGE and subsequently electrophoretically transferred onto PVDF membranes (Millipore, Darmstadt, Germany). After blocking in tris-buffered saline containing 0.1% of Tween20 (TBST) with 5% (w/v) skim milk (Nestle Carnation, New Zealand) for 2 h at room temperature, the membranes were incubated with primary and secondary antibodies and subsequently visualized with an enhanced chemiluminescence detection kit (Thermo Scientific™ SuperSignal™ West Pico Chemiluminescent Substrate, USA). β-Actin was used as the loading control for the experimental data analysis.

1.12. Molecular Modeling—ABCB1

In order to figure out the exact binding site for nobiletin, we used homology modeling and molecular docking to study the interaction between human P-Glycoprotein and nobiletin.

Human P-glycoprotein (ABCB1) was thought to have four sites interacting with the inhibitors, so we rebuilt the four sites using Prime v2.1 in Maestro 9.0 (Schrodinger, Inc., New York, N.Y., 2009). The 3D structures of ABCB1 from the mouse was selected as the templates: The complex structure cocrystallized with QZ59-RRR (PDB: 4M2S) for site 1, the complex structure cocrystallized with QZ59-SSS (PDB: 4M2T) for site 2, the apo structure (PDB: 3G5U) for site3 and site 4. The ligands from the complex templates were retained and used to define the site 1 and site 2 in the homology structures. The site 3 was defined by residues contributing to verapamil binding and the site 4 was defined by two residues which were common to the other three sites.

All the docking calculations for four sites were performed in the Induced Fit Docking module (Schrodinger, Inc., New York, N.Y., 2009) and the pose was ranked by the XP mode of Glide program v5.5 (Schrodinger, Inc., New York, N.Y., 2009). Then the pose with the highest docking were selected for further conformational analysis.

1.13 Statistical Analysis

Statistical analysis was carried out using Student's t-test or one-way analysis of variance with Microsoft Excel 2010, and the level of significance was set at a P value of <0.05(*), <0.01 () or <0.001(*). Data was expressed as the mean±SD.

2. Results 2.1 Demonstration of Multidrug Resistance in Cell Line Model

The $IC_{50}$ values of several anti-cancer drugs in parental line (A2780) and stably paclitaxel-resistant cell line (A2780/T) were determined. The mean $IC_{50}$ values for PTX and DOX were 501-fold and 158-fold greater in A2780/T cells than that of A2780, as shown in FIG. 2A and FIG. 2B, which confirmed that this cell line exerted much higher tolerance than the parental sensitive cell line. In FIG. 2C and FIG. 2D, RT-qPCR and Western blot analysis confirmed that the MDR1 gene and P-gp protein in the A2780/T were all significantly increased (p<0.01).

2.2 Sensitizing of ABCB1-Overexpressing Cells to Chemotherapeutic Agents by Nobiletin Firstly, the intrinsic cytotoxicity of nobiletin in A2780 and A2780/T was measured by the SRB assay. Nobiletin have similar $IC_{50}$ for both A2780 and A2780/T (without adding 0.94 μM PTX to culture medium), as shown in FIG. 2E. Notably, the results showed that nobiletin at 9 μM, showed no obvious cytotoxic effect to both cell lines, and more than 90% cells were viable. Based on this result, nobiletin was tested in the reversal assays at a maximum concentration of 9 μM.

Next, we tested whether nobiletin could reverse the MDR of A2780/T cells. Treatment with nobiletin significantly decreased the $IC_{50}$ of PTX and DOX in A2780/T cell in a concentration-dependent manner, as shown by the shift in the cytotoxicity curves to the left in FIGS. 3B and 3D. Specifically, as shown in Table 1, treatment with 0.5, 1.5, 4.5, and 9 μM nobiletin reduced the $IC_{50}$ of PTX in A2780/T cells by 3.0-, 18.5-, 163.5-, and 432.9-fold, respectively. The $IC_{50}$ of DOX was reduced 1.58-, 3.16-, 5.39- and 15.92-fold after combination treatment with 0.5, 1.5, 4.5, and 9 μM nobiletin, respectively. Meanwhile, nobiletin, at tested concentrations, had no effect on the $IC_{50}$ of PTX and DOX in parental non-resistant A2780 cells, as shown in FIGS. 3A and 3F. Moreover, at concentration of 4.5 μM, nobiletin also reduced $IC_{50}$ values of docetaxel and daunorubicin with reversal fold of 15.8 and 13.6, respectively, whereas it also slightly decreased the $IC_{50}$ values of 5-fluorouracil (non-substrate of ABCB1) with reversal fold of 6.3 as shown in Table 1.

TABLE 1

Nobiletin reverses the ABCB1-mediated drug resistance to 5-fluorouracil, docetaxel and doxorubicin in A2780/T cells.

| | A2780/T | |
|---|---|---|
| Drug | $IC_{50}$ ± SD (μM) | fold reversal |
| Paclitaxel | 2.67 ± 0.22 | 1.00 |
| +0.5 μM N | 0.90 ± 0.15*** | 3.00 |
| +1.5 μM N | 0.15 ± 0.02*** | 18.47 |
| +4.5 μM N | 0.02 ± 0.004*** | 163.46 |
| +9 μM N | 0.006 ± 0.0002*** | 432.98 |
| Docetaxel | 17.9 ± 2.89 | 1.00 |
| +0.5 μM N | 8.97 ± 1.46* | 2.05 |
| +1.5 μM N | 3.57 ± 0.58** | 5.01 |
| +4.5 μM N | 1.13 ± 0.18*** | 15.84 |
| Doxorubicin | 5.97 ± 0.49 | 1.00 |
| +0.5 μM N | 3.77 ± 0.30** | 1.58 |
| +1.5 μM N | 1.89 ± 0.16*** | 3.16 |
| +4.5 μM N | 1.13 ± 0.18*** | 5.39 |
| +9 μM N | 0.38 ± 0.04*** | 15.92 |
| Daunorubicin | 11.91 ± 0.97 | 1.00 |
| +0.5 μM N | 9.46 ± 0.77 | 1.26 |
| +1.5 μM N | 4.49 ± 0.73* | 2.70 |
| +4.5 μM N | 0.89 ± 0.15** | 13.58 |
| 5-Fluorouracil | 159.19 ± 18.30 | 1.00 |
| +0.5 μM N | 132.2 ± 23.78 | 1.21 |
| +1.5 μM N | 79.78 ± 9.18* | 1.99 |
| +4.5 μM N | 26.14 ± 1.77* | 6.08 |

TABLE 2

Nobiletin reverses the ABCB1-mediated drug resistance to 5-fluorouracil, docetaxel and doxorubicin in A549/T cells.

| | A549/T | |
|---|---|---|
| Drug | IC50 (μM) | Fold reversal |
| Paclitaxel | 1.89 ± 0.15 | 1.00 |
| +0.5 μM N | 0.75 ± 0.06* | 2.51 ± 0.01 |
| +1.5 μM N | 0.34 ± 0.02** | 5.65 ± 0.8 |
| +4.5 μM N | 0.09 ± 0.01*** | 22.33 ± 3.6 |
| +9 μM N | 0.03 ± 0.004*** | 62.88 ± 0.98 |
| Docetaxel | 13.36 ± 1.09 | 1.00 |
| +0.5 μM N | 8.43 ± 0.69* | 1.59 ± 0.01 |
| +1.5 μM N | 2.67 ± 0.22** | 5.05 ± 0.82 |
| +4.5 μM N | 0.71 ± 0.11** | 19.18 ± 4.59 |
| Doxorubicin | 5.97 ± 0.49 | 1.00 |
| +0.5 μM N | 4.23 ± 0.35 | 1.42 ± 0.23 |
| +1.5 μM N | 2.67 ± 0.22* | 2.25 ± 0.37 |
| +4.5 μM N | 1.19 ± 0.10** | 5.01 ± 0.01 |
| Daunorubicin | 10.07 ± 1.63 | 1.00 |
| +0.5 μM N | 5.97 ± 0.49* | 1.68 ± 0.14 |
| +1.5 μM N | 2.84 ± 0.46* | 3.55 ± 0.01 |
| +4.5 μM N | 0.71 ± 0.13** | 14.17 ± 0.04 |
| 5-Fluorouracil | 133.57 ± 10.86 | 1.00 |
| +0.5 μM N | 106.10 ± 8.63 | 1.26 ± 0.01 |

TABLE 2-continued

Nobiletin reverses the ABCB1-mediated drug resistance to 5-fluorouracil, docetaxel and doxorubicin in A549/T cells.

| | A549/T | |
|---|---|---|
| Drug | IC50 (μM) | Fold reversal |
| +1.5 μM N | 66.95 ± 5.44* | 1.99 ± 0.01 |
| +4.5 μM N | 16.82 ± 1.36** | 7.94 ± 0.02 |

In another ABCB1-overexpressing non-small cell human lung cancer cell line A549/T, which is also PTX-resistant, and its parental cells A549, it was observed that similar reversal effects of nobiletin to PTX. The intrinsic cytotoxicity of nobiletin in A549 and A549/T was also measured by the SRB assay. Nobiletin have similar $IC_{50}$ for both A549 and A549/T (without adding 0.94 μM PTX to culture medium), as shown in FIG. 2F. Notably, the results showed that nobiletin at 9 μM demonstrated no obvious cytotoxic effect to both cell lines, and more than 90% cells were viable. Based on this result, nobiletin was tested in the reversal assays at a maximum concentration of 9 μM.

In FIG. 3E, the treatment of nobiletin on A549 cell line at 0.5, 1.5, 4.5, and 9 μM significantly decreased the $IC_{50}$ of PTX with reversal fold of 2.51, 5.65, 22.33 and 62.88, respectively.

Moreover, at concentration of 4.5 μM, nobiletin also reduced $IC_{50}$ values of paclitaxel, docetaxel and daunorubicin with reversal fold of 22.33, 19.18 and 14.17, respectively, whereas it also slightly decreased the $IC_{50}$ values of doxorubicin and 5-fluorouracil (non-substrate of ABCB1) with reversal fold of 5.01 and 7.94, respectively, as shown in Table 2.

In order to determine whether the drug inhibition effect is related to the specific transport protein ABCB1, the inventors also tested the effect of quinidine (QND, an inhibitor of P-gp), MK571 (an inhibitor of MRPs) and KO143 (an inhibitor of BCRP) on inhibiting A2780/T cells to low-dose PTX-induced death. The fold-reversal of QND at concentration of 0.24, 0.72 and 2.16 μM to PTX was 3.25, 43.15, and 252.83, respectively, in A2780/T cells, as shown in FIG. 10A. But, QND showed an intimal cytotoxicity at concentration of 6.48 μM with only 40% cells survived. Moreover, MK571 and KO143 had no effects on the $IC_{50}$ of PTX which demonstrate that the reversal effect is special to ABCB1 transporter, as shown in FIG. 10B.

Moreover, the long term reversal effects of nobiletin on ABCB1 mediated MDR to PTX were evaluated using colony formation assays. Complete inhibition of colony formation can be achieved with the combination of 0.94 μM PTX with different concentrations of nobiletin, whereas no inhibition was observed for either 9 μM nobiletin or 0.94 μM PTX alone, as shown in FIG. 3C. Taken together, these results indicated that the combination of nobiletin and PTX elicits significantly higher cytotoxic response in ABCB1 overexpression MDR cancer cells.

In short, the results of this study suggest that nobiletin significantly sensitizes ABCB1-overexpressing cells to chemotherapeutic drugs that are substrates of ABCB1.

2.3 Potentiating PTX Induced Apoptosis in Resistant A2780/T Cells by Nobiletin

The inventors next investigated whether nobiletin increased the PTX-induced apoptosis in A2780 and A2780/T cells using double staining method. Consistent with its ability to inhibit cell growth, treatment with 0.5, 1.5, 4.5, and 9 μM nobiletin could significantly increase apoptosis induced by 0.94 μM PTX in a concentration-dependent manner, as shown in FIG. 4A. The inventors found that treatment with only 0.5 μM nobiletin could boost the apoptosis induced by PTX (0.94 μM) to a similar degree as that of 2.51 μM PTX ($IC_{50}$). While single treatment of 9 μM nobiletin or 0.94 μM PTX alone did not show apoptosis induction.

To further confirm these results, the inventors examined the well-established biochemical markers of cell cycle arrest and apoptosis: p53. Consistent with cell growth inhibition and apoptosis, treatment of PTX in combination with nobiletin resulted in accumulation of p53 in treated cells. The results were shown in FIG. 8B.

2.4 Arrest of Resistant Cells in G2/M-Phase by Nobiletin-PTX Combination

In this study was, the inventors investigated whether the effect of nobiletin causing G2/M cell cycle arrest is related to their observed synergistic effect between nobiletin and PTX. The results of this study were illustrated in FIGS. 4A and 4B.

Asynchronously growing A2780/T cells and its sensitive parental cell line A2780, treated with PTX in absence and presence of nobiletin, were examined for their cell cycle progression by flow cytometry. In untreated control, the percentage of A2780 cells in $G_0/G_1$-, S- and $G_2/M$ phases were 71.6%, 7.76% and 18.27%, respectively, while the percentage of A2780/T cells in $G_0/G_1$-, S- and $G_2/M$ phases were 66.13%, 6.25% and 24.77%, respectively. For A2780 cells, single exposure (24, 48, and 72 hours) with PTX (0.01 μM) resulted in G2 arrest, manifested by an increased G2-M content (31.9%, 63.2% and 80.07%), and decreased G1 phase content (46.47%, 15.57% and 5.53%, respectively) as shown in FIG. 4B.

In the absence of nobiletin treatment, there were 72% G1 phase and 17% G2 phase cells incubated with 0.94 μM PTX, whereas this distribution significantly shifted to 9.6% G1 and 75.77% G2 phase cells after treatment of nobiletin at 9 μM in combination with 0.94 μM PTX as further illustrated in FIG. 4B. This pattern was evidenced after 24 h and persisted over the 72 h of treatment (N.B. such data was not shown in FIG. 4). Also shown in FIG. 4B, a notable G2/M arrest was observed even with the lowest concentration of nobiletin tested (0.5 μM). Thus, while A2780/T cells were remarkably resistant to 0.94 μM PTX, which means that PTX alone has no cell cycle effect thereon, the combination of nobiletin with PTX was found to greatly increase the proportion of G2/M arrested cells to above 75%. However nobiletin of 9 μM alone had no effect on the cell cycle of A2780/T.

2.5 Evaluation of Combinational Effects of Nobiletin and PTX

The combinational cytotoxic effect of nobiletin with PTX in A2780/T cells was further evaluated using the Median Effect methods described by T-C Chou and P. Talalay. The combination index (CI) values calculated at 50% (ED50) and 90% ($ED_{90}$) cell kill were 0.013 and $5.14 \times 10^{-5}$ as shown in Table 3, indicating very strong synergistic cytotoxic effect (CI<0.1) for combinations of nobiletin (denoted as 'N' in Table 3) with PTX in the ABCB1-overexpressing A2780/T cells. With CalcuSyn simulation, an $ED_{50}$ is produced by 35.96 μM nobiletin or 4.20 μM PTX in A2780/T cells, but a combination of agents will produce this $ED_{50}$ at 0.022 μM PTX with 0.286 μM nobiletin, a 200-fold decrease for the $ED_{50}$ dose of PTX (Table 3). The quantitative diagnostic graphics for the synergistic effect between nobiletin (N) and paclitaxel (T) were shown in FIGS. 12A to 12D.

TABLE 3

The calculated CI for combination of nobiletin and paclitaxel as well as the simulated synergism dose at Fa 0.5 (ED50)

| Data for Fa = 0.5 | CI value | Dose N (μM) | Dose PTX (μM) |
|---|---|---|---|
| N | | 35.9574 | |
| PTX | | | 4.20446 |
| N + PTX | 0.01334 | 0.28572 | 0.02268 |

CI analyses of the effects of nobiletin in combination with paclitaxel are shown. The CI values were plotted as a function of the particular inhibitory effect. CI values <1 represent a synergistic combination, CI values equal to 1 indicate an additive effect whereas CI values >1 represent antagonistic combinations. It can be concluded from the table that PTX was significantly reduced in nobiletin treated A2780/T cells.

In short, this evaluation study confirms the synergistic effect in the combinational use of nobiletin and PTX in cancer treatment.

2.6 Increase of the Intracellular Accumulation of DOX and Flutax-2 by Nobiletin

The above results proved that nobiletin have a significant effect on reversing ABCB1-mediated MDR. At present, the mechanism of this phenomenon is unknown. Therefore, the inventors conducted assays to examine the effect of nobiletin on the accumulation of DOX, and Flutax-2 (a fluorescent taxol derivative) in A2780 cells and their corresponding ABCB1-overexpressing A2780/T cells.

The inventors studied the effect of nobiletin on the intracellular accumulation of DOX and Flutax-2 using fluoresce microscope and flow cytometry analysis. The intracellular accumulation of DOX and Flutax-2 were significantly higher in A2780 than that in A2780/T, as shown in FIGS. 5A to 5D. When the drug-resistant cells were treated with 4.5 μM nobiletin or 20 μM QND (positive control), the intracellular accumulation of DOX (as shown in FIG. 5A), and Flutax-2 (as shown in FIG. 5C) were higher than that in untreated A2780/T. In contrast, nobiletin alone had no effect on DOX and Flutax-2 levels in the parental A2780 cells. With flow cytometry analysis, the enhanced intracellular accumulation of DOX, or Flutax-2 by nobiletin were further confirmed as shown in FIGS. 5B and 5D.

Taken together, these results showed that nobiletin significantly increased the intracellular accumulation of chemotherapeutic drugs in ABCB1-overexpressing cells, thus increasing the cytotoxicity to these MDR cells. In other words, nobiletin is shown to enhance the efficacy of DOX or PTX in cancer treatment.

2.7 Inhibition of the Efflux Activity of ABCB1 Transporter in Caco-2 Cells by Nobiletin Human colorectal carcinoma Caco-2 cells are widely used as an in vitro model for predicting human drug absorption and efflux activity of transporters. To further confirm the effect of nobiletin on P-gp function, the inventors evaluated the concentrations of the P-gp substrates Rho 123, DOX, and Flutax-2 in the presence or absence of nobiletin using the Caco-2 monolayer model.

Figure 11A:
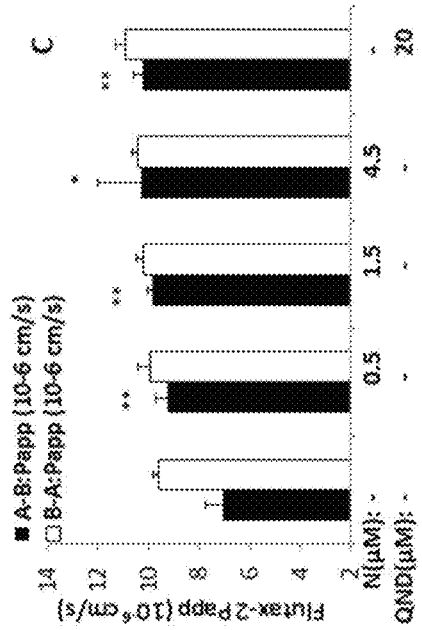
Figure 11B:
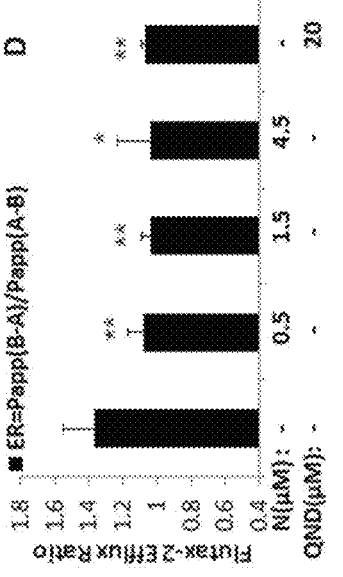
Figure 11C:
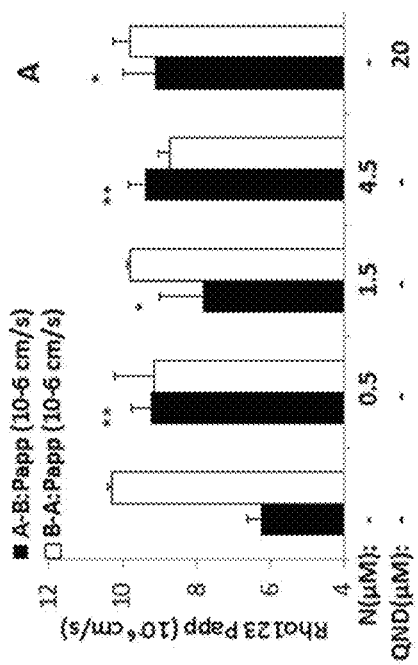
Figure 11D:
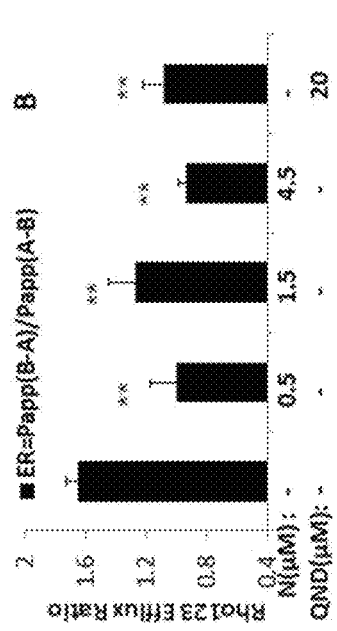

Two hours after administration, the values of $P_{app}$ (A-B) of DOX (as shown in FIG. 6A), Rho 123 (as shown in FIGS. 11A and 11B), and Flutax-2 (as shown in FIGS. 11C and 11D) was increased in the presence of nobiletin in a dose-dependent fashion; moreover, the efflux ratio (the ratio between the $P_{app}$ from the BL to the AP side and that from the AP to the BL side) was decreased in an nobiletin concentration dependent manner. As shown in FIG. 6B, the efflux ratio of DOX was decreased about 3.23-, 3.75- and 4.6-fold with nobiletin concentration of 0.5, 1.5, 4.5 μM. Intriguingly, the inhibitory effect of nobiletin at 4.5 μM was stronger than that of QND (20 μM) which was used as positive control.

These results were in agreement with the notion that nobiletin increased Rho 123, DOX, and Flutax-2 accumulation in resistant ABCB1-overexpressing cells by inhibiting ABCB1 transporter.

In short, the decrease of efflux ratio of DOX in the presence of nobiletin suggested that nobiletin is shown to increase absorption of DOX into Caco-2 cells by effecting the ABCB1 transporter function.

2.8 Activation of the ATPase Activity of ABCB1 by Nobiletin

The efflux function of ABCB1 has a close relationship with ATP hydrolysis. Therefore, the inventors measured ABCB1-mediated ATP hydrolysis with different concentrations of nobiletin. As shown in FIG. 7A, nobiletin stimulated the ATPase activity of ABCB1 in a dose-dependent manner, with $EC_{50}$ of 5.88 μM and a maximal stimulation of 3-fold of the basal activity, suggesting that nobiletin affected the ATPase activity of ABCB1 and might interact at the drug-substrate-binding site as a substrate of ABCB1.

To characterize inhibition effect of nobiletin on P-gp ATPase activity, the inventors also examined the effects of nobiletin on verapamil stimulated P-gp ATPase activity. Verapamil is sometimes referred as a P-gp inhibitor because as a substrate for transport it inhibits P-gp activity with other substrates by interfering with their transport in a competitive mode. FIG. 6B showed the reduction of 200 μM verapamil-stimulated ATPase activity by nobiletin with an $IC_{50}$ value of 7.17 μM, indicating nobiletin is a P-gp ATPase inhibitor.

2.9 Mechanism of Reversal of ABCB1-Mediated MDR by Nobiletin

The reversal of ABCB1-mediated MDR can be achieved either by reducing ABCB1 expression or by inhibiting the function of ABCB1 transporter. Therefore, the inventors investigated the effect of nobiletin on the expression of ABCB1 at both mRNA and protein level.

At the selected concentrations used in the reversal assays, nobiletin did not significantly alter the expression of MDR1 mRNA, as shown in FIG. 8A, or protein level of ABCB1, as shown in FIG. 8B in A2780/T cells. These findings revealed that the MDR reversal effect of nobiletin was not due to the inhibition of ABCB1 expression. Therefore, the result suggested that the inhibition of ABCB1 transporter function appears to be the mechanism of sensitization of ABCB1-overexpressing MDR cells by nobiletin could be, and such inhibition leads to an increase in intracellular accumulation of chemotherapeutic drugs.

2.10 Inhibition of the Phosphorylation of AKT/ERK/Nrf2 by Nobiletin-PTX Combination Moreover, nobiletin was reported to inhibit phosphorylation of AKT and phosphorylation of ERK2 in HGF-treated liver cancer HepG2 cells. Considering the up-regulation of PI3K/AKT and MAP kinase/ERK pathways in resistance MDR cancer cells, hence, the inventors examined the effect of nobiletin on the expression of the total and phosphorylated AKT and ERK in A2780/T cells.

After treatment with PTX and nobiletin for 48 h, there was significant inhibitory effect on phosphorylated AKT and ERK, but not on total AKT and ERK (as shown in FIG. 8B), indicating the inhibition of PI3K/AKT and MAP kinase/ERK pathways by the combinational treatment. Moreover, there was a significant decrease for the phosphorylated AKT/ERK level after treatment with 50 μM nobiletin as shown in FIG. 8B. However nobiletin alone at reversal concentrations had no effect on the expression of the total and phosphorylated AKT and ERK as shown in FIG. 13. These results indicated that enhanced cytotoxic response by co-treatment with nobiletin and PTX in ABCB1 overexpression MDR cancer cells is associated with inhibition of PI3K/AKT and MAP kinase/ERK pathways.

Nuclear factor E2-related factor 2 (Nrf2) is a transcription factor that upregulates expression of a battery of genes to combat oxidative and electrophilic stress. Recent studies reveal that activation of the Nrf2 overexpression enhances chemoresistance, whereas blockade of Nrf2 inhibits a variety of cancer cells. In this study, the inventors observed a remarkably higher level of Nrf2 in A2780/T cells as compared with A2780 cells as shown in FIG. 8C. Nobiletin in combination with 0.94 µM PTX reduced the protein level of Nrf2 in a dose-dependent manner. These results clearly demonstrate that nobiletin is a potent small-molecular inhibitor of Nrf2.

2.11 Molecular Docking Simulation of Nobiletin within the Drug Binding Cavity of ABCB1

To understand the binding mechanism of nobiletin to homology model 28 of human ABCB1 at molecular level, the inventors performed glide docking using ABCB1-QZ59-RRR (site-1), ABCB1-QZ59-SSS (site-2), ABCB1-verapamil (site-3), and site common to above three sites (site-4) and ATP binding site. According to the docking result, the poses of nobiletin was only accommodated to site 1 with Docking score (Kcal/mol) at −9.216. There were no poses suitable for nobiletin to other three sites. Thus, site 1 was the only rational site for nobiletin.

As shown in FIG. 9A, the binding site of nobiletin was partially superposed with the binding site of QZ59-RRR known as Site 1. The ring-a of nobiletin substituted with four methoxyl groups was mainly engaged in hydrophobic contacts with Tyr307, Phe303, Tyr310, Phe335, Leu339, Leu336, Leu332. The methoxy of ring-a and the carbonyl of ring-b formed hydrogen bonds with Tyr307 and Gln725 respectively, which also appeared in the binding of vardenafil and tadalafil. As for ring-c, the hydrophobic contacts with Phe732, Phe971, Ser970, Ile78, Met75, Tyr953, Val71 kept the conformation stable.

3. Discussion

Traditional chemotherapy drugs such as PTX remain the cornerstone of tumor therapy, but the occurrence of drug resistance has been a major obstacle leading to the failure of tumor treatment. A number of different mechanisms were found to mediate the development of MDR, including overexpression of ABC transporters, activation of PI3K/AKT, MAP kinase/ERK and Nrf2 pathways. ABCB1 (P-gp) has been demonstrated to be an essential MDR transporter along with some relatives of the ABC family transporters (like ABCG2, ABCC1 and ABCC10) for several major chemotherapeutic drugs. In the past thirty years, great efforts have been made to search for the ABCB1 inhibitors. The three generation of ABC modulators such as quinine, verapamil, cyclosporine-A, tariquitor, PSC 833, LY335979, and GF120918 required high doses to reverse MDR and were associated with adverse effects. Currently, discoveries of more efficacious, non-toxic and less expensive compounds from natural products to reverse MDR are gaining increasing interests.

The inventors found that nobiletin was found to restore the cytotoxicity of PTX in ABCB1-expressing A2780/T cells. Pilot studies in small-animal and human clinical trials indicated nobiletin had a favorable safety profile without adverse events and significant effects in reducing total cholesterol, improving blood lipid profile. The peak plasma level of nobiletin was ~2.5 µM in healthy subjects after single dose of Sytrinol (containing 1053 mg of total polymethoxylated flavones) and ~22.5 µM in rats after single administration of 50 mg/kg of body weight by gavage. Upon considering the appropriate structure, safety, multiple modes of action and outstanding activity based on inventors' primary screening data, the inventors investigated if nobiletin could inhibit the ABCB1-overexpression MDR cancer cells to chemotherapeutic agents and the underlying mechanisms.

In this study, nobiletin at non-cytotoxic concentrations significantly increased the sensitivity of ABCB1 overexpressing A2780/T, and A549/T cell lines to chemotherapeutic agents such as DOX, PTX, docetaxel and dounorubicin, whereas it cannot potentiate the effect of these substrate drugs on parental cells as shown in FIG. 3A. A significant decrease in the $IC_{50}$ values of PTX (about 432 fold) was observed for the first time by co-treatment with PTX and nobiletin. In accordance with that of the cytotoxicity assay, it was found that nobiletin remarkably enhanced the intracellular accumulation of DOX and flutax-2 in drug resistant cells but not parental sensitive cells, indicating nobiletin might affect the ABCB1 function as shown in FIGS. 4A and 4B. Moreover, it was demonstrated that nobiletin could inhibit the efflux activity of ABCB1 transporter in Caco-2 monolayer cell model, which was shown in FIGS. 5A to 5D. Importantly, the concentrations of nobiletin used in this study were lower than the maximal plasma concentration (22.5 µM) obtained in vivo pharmacokinetic study of nobiletin.

It has been reported that PTX exerts cytotoxicity by inhibiting mitotic progression and arresting cells in mitosis (G2/M phase), while nobiletin also could induce apoptosis and block the cell cycle arrested at G2 phase. Thus, the inventors investigated the contribution of nobiletin to the observed enhanced cytotoxicity in MDR cells after co-treatment with both PTX and nobiletin. In this study, nobiletin at non-cytotoxic concentrations promoted cell apoptosis induced by paclitaxel as shown in FIG. 4A in a p53-dependent manner as shown FIG. 8B. Moreover, upon co-treatment with nobiletin and PTX, a notable reduction in the fraction of cell in the G0/G1, and a significant accumulation of cells in the G2/M phase (>75%) were found for A2780/T cells; the result was shown in FIG. 4B. These data suggested the boosted cytotoxicity after co-treatment of nobiletin and PTX could be due to the intracellular accumulation of PTX. In addition, the combination studies indicated that nobiletin is a very strong synergist for enhancing the anti-tumor effect of PTX in MDR cancer cell lines, and it was predicted that 0.286 µM nobiletin could bring a 200-fold decrease on the $ED_{50}$ of PTX. In short, the inventor concludes that nobiletin decreased the transporter activity of ABCB1, thus enhancing the intracellular drug concentration, and the finding that nobiletin enhanced the overall cytotoxicity of these drugs is consistent with the higher intracellular drug accumulation.

As energy used by ABCB1 transporter comes from ATP hydrolysis, the inventors also investigated the ATPase activity of ABCB1 transporter to confirm their previous assumption. As the activity of ATPase was stimulated by nobiletin in a concentration dependent manner, nobiletin might potentially be a substrate of ABCB1. Moreover, verapamil-stimulated ATPase activity was reduced by nobiletin. Therefore, it may competitively bound to the substrate-binding site of ABCB1, leaving little room for other agents to bind to the transporter, which resulted in decreased activity of ABCB1 transporter. The MDR reversal effect can be achieved either by reducing ABCB1 expression or by inhibiting the efflux ability of ABCB1 transporter. Therefore, the inventors also examined the effect of nobiletin on the expression of MDR1 mRNA and ABCB1 protein. However, nobiletin did not affect the ABCB1 expression in both mRNA and protein levels at the reversal concentrations as shown in FIGS. 8A to 8C.

Moreover, previous pre-clinical and clinical evidence suggested that the PI3K/AKT, MAPk/ERK and Nrf2 signaling pathways were associated with resistance to multiple chemotherapeutic drugs. Inactivating the AKT/ERK and Nrf2 signaling pathway renders MDR cancer cells more sensitive to drugs such as paclitaxel, doxorubicin, 5-fluorouracil, etc. As nobiletin has been demonstrated with an inhibition effect on the phosphorylation of AKT and ERK, therefore, the inventors evaluated the effect of nobiletin on AKT/ERK phosphorylation in A2780/T cells using Western Blot analysis. As shown in FIG. 8B, nobiletin-PTX co-treatment reduced phosphorylated AKT/ERK, which indicated that the inhibition of AKT/ERK also accounts for the inhibiting effect of nobiletin in MDR-cancer cells. Moreover, co-treatment of nobiletin-PTX significantly suppressed Nrf2 expression in A2780/T cells in which the A2780/T cells have a significantly higher level of Nrf2 than that of A2780 cells. These findings may not only be helpful for illustrating the multiple mechanisms behind the reversal effect of nobiletin, but also helpful for explaining the reversal effect of nobiletin to 5-fluorouracil which is not a P-gp substrates. Literature has demonstrated that the inhibition of Nrf2 expression could go through PI3K/AKT and ERK signaling pathway. Thus, mechanistically, nobiletin inhibits the MDR cancer cells to chemotherapeutic agents could through significantly reduced Nrf2 expression and down-regulated PI3K-Akt and ERK pathway.

In order to further study the interaction between nobiletin and ABCB1 transporter, the inventors conducted the docking analysis with human ABCB1 homology model. The predicted binding conformation of nobiletin within the large hydrophobic drug binding cavity (Site-1) of human ABCB1 shows the major contributions of hydrophobic interactions as shown in FIGS. 9A to 9C. The methoxyl and aromatic ring are important for interaction with the drug-binding cavity of ABCB1 transporters. Overall, docking simulation will be useful for understanding ligand-protein interactions and for future optimizing derivatives.

In conclusion, this study provided the first evidence that nobiletin significantly reversed ABCB1 mediated MDR by inhibiting the efflux function of ABCB1 transporter and suppressing the chemoresistance related AKT/ERK/Nrf2 pathways. As a very strong synergist, nobiletin promoted cell apoptosis as well as G2/M cell cycle arrest induced by PTX and reduced $EC_{50}$ value of PTX. In addition, the reversal effect of nobiletin was independent of inhibiting ABCB1 expression. Given the broad-spectrum organ safety of nobiletin which has been demonstrated in laboratory animals in vivo, this invention suggests that nobiletin as combination therapy may be a good candidate for studies in vivo and could be a clinically useful drug to reverse ABCB1-medicated drug resistance in cancer therapy.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example, one skilled in the art could appreciate that to achieve the synergistic effect mentioned in Section 2.5, the nobiletin could be applied together with PTX, or before/after PTX treatment.

What is claimed is:

1. A method of treating multidrug resistance cancer, comprising:
   administering a pharmaceutically effective amount of a citrus methoxyflavone and a chemotherapeutic drug to a subject in need thereof,
   wherein the citrus methoxyflavone is nobiletin, the chemotherapeutic drug is paclitaxel, and the multidrug resistance cancer is paclitaxel-resistant ovarian cancer;
   wherein the paclitaxel and the nobiletin are administered to the subject in a molar ratio of 0.94:0.5 to 0.94:9 to treat the paclitaxel-resistant ovarian cancer.

2. The method of claim 1, wherein the nobiletin can inhibit function of ABCB1 transporter such that intracellular accumulation of the paclitaxel is increased.

3. The method of claim 1, wherein the molar ratio of the paclitaxel to the nobiletin is selected from a group consisting of 0.94:0.5, 0.94:1.5, 0.94:4.5, and 0.94:9.

4. The method of claim 1, wherein the paclitaxel and the nobiletin are simultaneously administered to the subject.

5. A method of enhancing an efficacy of a chemotherapeutic drug to treat multidrug resistance cancer, comprising:
   administering the chemotherapeutic drug to a subject; and
   applying a citrus methoxyflavone to the subject,
   wherein the citrus methoxyflavone is nobiletin, the chemotherapeutic drug is paclitaxel, and the multidrug resistance cancer is paclitaxel-resistant ovarian cancer;
   wherein the paclitaxel and the nobiletin are administered to the subject in a molar ratio of 0.94:0.5 to 0.94:9 to treat the paclitaxel-resistant ovarian cancer.

6. The method of claim 5, wherein the nobiletin can inhibit function of ABCB1 transporter such that intracellular accumulation of the paclitaxel is increased.

7. The method of claim 5, wherein the molar ratio of the paclitaxel to the nobiletin is selected from a group consisting of 0.94:0.5, 0.94:1.5, 0.94:4.5, and 0.94:9.

8. The method of claim 5, wherein the paclitaxel and the nobiletin are simultaneously administered to the subject.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Forward primer for MDR1

<400> SEQUENCE: 1
gagagatcct caccaagcgg                                          20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for MDR1

<400> SEQUENCE: 2
cgagcctggt agtcaatgct                                          20

<210> SEQ ID NO 3
<211> LENGTH: 20
<212> TYPE: DNA
<213> ORGANISM: Artificial Sequence
<220> FEATURE:
<223> OTHER INFORMATION: Forward primer for TIF
```

```
<400> SEQUENCE: 3
agaaggctgg ggctcatttg                                               20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for TIF

<400> SEQUENCE: 4
aggggccatc cacagtcttc                                               20
```